US008614345B2

(12) United States Patent
Santoro et al.

(10) Patent No.: US 8,614,345 B2

(45) Date of Patent: Dec. 24, 2013

(54) HYDROGENATION OF ESTERS OR CARBONYL GROUPS WITH TETRADENTATE AMINO/IMINO-THIOETHER BASED RUTHENIUM COMPLEXES

(75) Inventors: Francesco Santoro, Geneva (CH); Lionel Saudan, Geneva (CH); Christophe Saudan, Geneva (CH); Michel Alfred Joseph Saudan, legal representative, Geneva (CH); Sylvia Joyeuse Adélaïde Ada Saudan, legal representative, Geneva (CH)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 13/996,847

(22) PCT Filed: Dec. 19, 2011

(86) PCT No.: PCT/EP2011/073223

§ 371 (c)(1), (2), (4) Date: Jun. 21, 2013

(87) PCT Pub. No.: WO2012/084810

PCT Pub. Date: Jun. 28, 2012

(65) Prior Publication Data

US 2013/0274487 A1 Oct. 17, 2013

(30) Foreign Application Priority Data

Dec. 21, 2010 (EP) .................................... 10196140

(51) Int. Cl.

| | |
|---|---|
| ***C07F 15/00*** | (2006.01) |
| ***C07C 29/141*** | (2006.01) |
| ***C07C 29/145*** | (2006.01) |
| ***C07D 317/54*** | (2006.01) |

(52) U.S. Cl.

USPC ............ 556/32; 556/137; 568/814; 568/819; 568/823; 568/824; 568/838; 549/445

(58) Field of Classification Search

USPC ............ 556/32, 137; 549/445, 503; 568/814, 568/819, 823, 824, 838

See application file for complete search history.

(56) References Cited

FOREIGN PATENT DOCUMENTS

| | | | |
|---|---|---|---|
| EP | 0 901 997 | B1 | 3/1999 |
| EP | 1 813 621 | B1 | 8/2007 |
| WO | WO 01/23088 | A1 | 4/2001 |
| WO | WO 02/22526 | A2 | 3/2002 |
| WO | WO 02/40155 | A1 | 5/2002 |
| WO | WO 2008/065588 | A1 | 6/2008 |

OTHER PUBLICATIONS

International Search Report and Written Opinion, application No. PCT/EP2011/073223, mailed Mar. 26, 2012.
D. A. Nation et al., Journal of the Chemical Society, Dalton Trans., No. 14, 1996, pp. 3001-3009.
He et al., Org. Biomol. Chem., 2010, 8, pp. 2497-2504.
Hedberg et al., JACS, 2005, 127, pp. 15083-15090.
Ito et al., Organometallics, 2001, 20, pp. 379-381.
Blum et al., Organometallics, 1985, 4, pp. 1459-1461.
Vicente et al., Journal of Molecular Catalysis A.: Chemical, 98, 1995, L5-L8.
Bohle et al., Inorg. Chem., 2000, 39, pp. 712-718.
Nakajima et al., Inorganica Chimica Acta, 274, 1998, pp. 184-191.
Powell et al., J. Chem. Soc. (A), 1968, pp. 159-161.
Albers et al., Inorganic Synth., 1989, 26, pp. 249-258.
Schrock et al., Chem. Soc. Dalton Trans., 1974, 9, pp. 951-959.

*Primary Examiner* — Bernard Dentz

(57) ABSTRACT

The present invention relates to the field of catalytic hydrogenation and, more particularly, to the use of specific ruthenium catalysts, or pre-catalysts, in hydrogenation processes for the reduction of ketones and/or aldehydes into the corresponding alcohol respectively. Said catalysts are ruthenium complexes comprising a tetradentate ligand (L4) coordinating the ruthenium with: —two nitrogen atoms, each in the form of a primary or secondary amine (i.e. a $NH_2$ or NH group) or N-alkyl imine functional groups (i.e. a C═N group), and —two sulfur atoms, each in the form of thioether functional groups.

9 Claims, No Drawings

HYDROGENATION OF ESTERS OR CARBONYL GROUPS WITH TETRADENTATE AMINO/IMINO-THIOETHER BASED RUTHENIUM COMPLEXES

TECHNICAL FIELD

The present invention relates to the field of catalytic hydrogenation and, more particularly, to the use of specific ruthenium catalysts, or pre-catalysts, in hydrogenation processes for the reduction of ketones or aldehydes into the corresponding alcohols.

PRIOR ART

The reduction of the C═O bond in a ketone or aldehyde functional group to the corresponding alcohol is one of the fundamental reactions in organic chemistry, and is used in a large number of chemical processes. In general, three kinds of processes are known to achieve such a transformation:

a) hydride processes, in which a silyl or metal hydride salt, such as $LiAlH_4$, or PMHS (polymethylhydrosiloxane) is used;

b) hydrogen transfer processes, in which a dihydrogen donor (such as HCOOH or $^{i}$PrOH) is used;

c) direct hydrogenation processes, in which molecular hydrogen is used.

From a practical point of view, hydrogenation processes are more attractive as compared to hydride processes, or hydrogen transfer, as they can be run using small amounts of catalyst (typically 10 to 1000 ppm relative to the substrate), do not require the use of highly reactive and expensive hydrides or high dilutions conditions, and do not generate important amounts of aqueous waste. Moreover, direct hydrogenation processes are even more desirable as they can be carried out in the presence of small quantities or even in the absence of solvent.

One of the mandatory and characterizing elements of direct hydrogenation processes is the catalyst or the catalytic system that is used to activate the molecular hydrogen to promote of the reduction. The development of useful catalysts or catalytic systems for the hydrogenation of a ketone, aldehyde or ester functional group represents an important, difficult, and unpredictable task in chemistry.

To the best of our knowledge, the most efficient ruthenium catalysts or catalytic systems known to perform direct hydrogenations are based on complexes containing ligands possessing at least one coordinating phosphorus atom, the best systems having a $P_2N_2$ coordination sphere. Typical examples are the (PP)(NN) type (see EP 0901997 and EP 1813621 for ketones and aldehydes, or more recently WO08/065,588 for esters), or (PN)(PN)/($P_2N_2$) type (see WO02/022526 or WO02/40155).

However, such catalysts suffer from the fact that the syntheses of phosphorous-containing ligands are tedious, they often require the use of oxygen and water-free conditions, and generate important amounts of waste. Most importantly, phosphines can be easily oxidized and their sensitivity towards oxygen is often transmitted to the corresponding complexes with deleterious consequences for their catalytic activities. These phosphorous-containing ligands are also generally expensive.

It is therefore desirable to have catalysts bearing phosphorous-free ligands (see Yan-Mei He, et al. *Org. Biomol. Chem.*, 2010, 8, 2497).

Some phosphorous-free catalysts are known from the prior art, [Andersson, JACS 2005, 127, 15083 (RuCp or Cp*); Ikariya, Organometallics 2001, 20, 379 (RuCp*); Shvo, Organometallics 1985, 4, 1459 (Ru-cyclopentadienone); Chaudret, J. Mol. Catal. A. Chem. 1995, 98, L5 (Ru-Pyrazolylborane)]. However these systems are all organometallic cyclopentadienyl half-sandwich complexes or contain isolobal ligands (such as boron-tripodal ligands) and therefore suffer from being expensive, sensitive to the external conditions, and having a very limited, if any, capacity to be derivatized in order to tune the selectivities or the reactivity.

In view of the above, there is a need for direct hydrogenation processes using catalysts or pre-catalysts bearing phosphorous-free ligands that are cheaper and handier and that can provide for a greater structural diversity to allow a straightforward tuning of the steric and electronic properties of the catalyst.

We have now found that Ru complexes having the metal centre coordinated by two nitrogen atoms and two sulfur atoms (i.e. tetradentate ligands without coordinating phosphorous atoms) can be used as catalyst or pre-catalyst in the direct hydrogenation of ketone or aldehyde groups. These ligands are cheap, much less sensitive toward oxidation than phosphines and allow a great structural diversity. To the best of our knowledge, there is no report or suggestion in the prior art of the present invention.

In fact, the only examples of reduction of ketone or aldehyde group into the corresponding alcohol by means of complexes having the metal centre coordinated by nitrogen atoms and sulfur atoms are reported in WO 01/23088. However in said document the number of coordinating ligands is unknown and it describes only a hydrogen transfer process, which is fundamentally different from a direct hydrogenation according to the invention (the reducing agent being completely different).

DESCRIPTION OF THE INVENTION

In order to overcome the problems aforementioned, the present invention relates to processes for the reduction by hydrogenation, using molecular $H_2$, of a $C_3$-$C_{70}$ substrate containing one, two or three ketones and/or aldehydes functional groups into the corresponding alcohol, characterized in that said process is carried out in the presence of at least a base and at least one catalyst or pre-catalyst in the form of a $C_8$-$C_{56}$ ruthenium complex comprising in the coordination sphere a tetradentate ligand (L4) coordinating the ruthenium with:

- two nitrogen atoms, each in the form of a primary or secondary amine (i.e. a $NH_2$ or NH group) or N-alkyl imine functional groups (i.e. a C═N group), and
- two sulfur atoms, each in the form of thioether functional groups.

According to a particular embodiment of the invention, the substrate can be a $C_{3-30}$ compound, in particular of formula of formula (I)

(I)

$$R^a\text{–C(=O)–}R^b$$

wherein $R^a$ represents a hydrogen atom or a $R^b$ group; and $R^b$ represents a $C_1$-$C_{29}$ hydrocarbon group optionally substituted and optionally comprising one or two carbonyl groups, a $C_1$-$C_6$ hydrocarbon group substituted by a $C_{3-8}$ heterocycle (aromatic or not) comprising one or two atoms selected amongst sulfur, nitrogen or oxygen, or a $C_{3-8}$ heterocycle (aromatic or not) comprising one or two atoms selected amongst sulfur, nitrogen or oxygen optionally substituted by one or two $C_1$-$C_6$ hydrocarbon group;

$R^a$ and $R^b$ are bonded together and form a $C_3$-$C_{20}$, preferably $C_4$-$C_{20}$, saturated or unsaturated hydrocarbon group, optionally substituted and optionally comprising one or two carbonyl groups.

According to a particular embodiment of the invention, the substrate can be a $C_{3-30}$ compound, in particular of formula of formula (I)

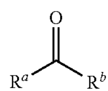

(I)

wherein $R^a$ represents a hydrogen atom or a $C_1$-$C_{28}$ hydrocarbon group, optionally substituted; and $R^b$ represents a $C_1$-$C_{29}$ hydrocarbon group, optionally substituted and optionally comprising one or two carbonyl groups; or represents a $C_{3-8}$ heterocycle (aromatic or not) comprising one or two atoms selected amongst sulfur, nitrogen or oxygen;

$R^a$ and $R^b$ are bonded together and form a $C_3$-$C_{20}$, preferably $C_4$-$C_{20}$, saturated or unsaturated hydrocarbon group, optionally substituted and optionally comprising one or two carbonyl groups.

In a particular embodiment of the invention, said $R^b$ group comprises zero or one carbonyl group.

The corresponding alcohol, the product obtained with the invention's process, is of formula

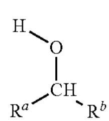

(II-a)

wherein $R^a$ and $R^b$ are defined as in formula (I).

It is understood that said compounds (II-a) can be in a racemic or optically active form, depending on the nature of the substrate and on the catalyst/pre-catalyst used.

It is understood that by " . . . hydrocarbon group . . . " it is meant that said $R^a$ or $R^b$ can be in the form of a linear, branched or cyclic aromatic, alkyl, alkenyl, or alkynyl group, e.g., a linear alkyl group, or can also be in the form of a mixture of said type of groups, e.g. a specific $R^a$ may comprise a linear alkyl, a branched alkenyl (e.g. having one or more carbon-carbon double bonds), a (poly)cyclic alkyl and an aryl moiety, unless a specific limitation to only one type is mentioned. Similarly, in all the below embodiments of the invention, when a group is mentioned as being in the form of more than one type of topology (e.g. linear, cyclic or branched) and/or unsaturation (e.g. saturated, unsaturated or aromatic, or more particularly alkyl, aromatic or alkenyl), it is meant also a group which may comprise moieties having any one of said topologies or unsaturations, as explained above.

According to a further embodiment of the invention, the substrate is a ketone or aldehyde that will provide an alcohol that is useful in the pharmaceutical, agrochemical or perfumery industry as final product or as an intermediate. Particularly preferred substrate is a ketone or aldehyde that will provide an alcohol useful, as final product or as an intermediate, in the perfumery industry.

According to another embodiment of the invention, the substrate is a $C_3$-$C_{20}$, or a $C_5$-$C_{15}$, compound of formula (I), and in particular one may cite those wherein $R^a$ represent a hydrogen atom or a $R^b$ group, $R^b$ representing a linear, branched or cyclic $C_2$-$C_{19}$ hydrocarbon group optionally substituted; or $R^a$ and $R^b$ are bonded together and form a $C_5$-$C_{19}$ saturated or unsaturated hydrocarbon group, optionally substituted.

Possible substituents of IV and $R^b$ are one, two, or three halogen, $OR^c$, $NR^c_2$, $SR^c$, groups, in which $R^c$ is a hydrogen atom, a halogenated $C_1$-$C_2$ group or a $C_1$ to $C_{10}$ cyclic, linear or branched alkyl or alkenyl group, preferably a $C_1$ to $C_4$ linear or branched alkyl or alkenyl group.

According to a further embodiment of the invention, said substituents are one or two $OR^c$ groups, in which $R^c$ is a hydrogen atom or a $C_1$ to $C_6$ cyclic, linear or branched alkyl or alkenyl group.

Non-limiting examples of substrates are the following:

aldehydes:

a $C_{3-15}$ alkanal, a $C_{4-15}$ 3-methyl-2-alkenal, a $C_{10-18}$ 3-(un) substituted aryl-3-($C_{1-6}$ alkyl)-2-propenal, a $C_{10-18}$ 3-(un) substituted aryl-2-($C_{1-6}$ alkyl)-2-propenal, a $C_{10-18}$ 3-(un) substituted aryl-3-($C_{1-6}$ alkyl)-2-methyl-2-propenal, a $C_{4-15}$ conjugated or de-conjugated alkenal or alkdienal, a $C_{7-15}$ aldehyde comprising a (un)substituted aryl group, a $C_{5-10}$ (un)substituted aldehyde comprising an aromatic or non aromatic heterocycle comprising an oxygen or sulfur atom; and ketones:

a di-($C_{1-15}$ alkyl)ketone, a $C_8$-$C_{15}$ (un)substituted-benzyl alkyl ketone, a $C_8$-$C_{15}$ (un)substituted-styryl alkyl ketone, a $C_{12}$-$C_{15}$ ketone comprising a 2,6,6-trimethyl cyclohexenyl/cyclohexyl group, a $C_{13}$-$C_{15}$ ketone comprising a 2,2,3-trimethyl-cyclopentenyl or 2,2,3-trimethyl-cyclopentyl group, a $C_4$-$C_{12}$ (un)substituted cyclic ketone, a $C_{10-18}$ (un)substituted cyclopentenone or (un)substituted cyclopentanone alpha substituted by a $C_{5-12}$ hydrocarbon group, a $C_{11-18}$ (un)substituted cyclohexenone or cyclohexanone alpha substituted by a $C_{6-12}$ hydrocarbon group, a $C_{8-16}$ (un)substituted aryl alkyl ketone, a $C_{4-15}$ 1-alkene alkyl ketone, a $C_{4-15}$-1-alkyne alkyl ketone, a $C_{9-18}$ (un)substituted 1-indanone, a $C_{10-20}$ (un)substituted 1-tetralone, a $C_{10-20}$ (un)substituted 2-tetralone;

wherein by "(un)substituted" it is meant that said ketone or aldehyde can be substituted by one or more groups as above defined for $R^a$ or $R^b$;

wherein by "aryl" it is meant a phenyl or naphthyl group.

As mentioned above, the present invention requires the use of a particular Ru catalyst or pre-catalyst (Ru complex). Many Ru complexes can be used, but all have the same common point: i.e. a coordination sphere comprising a tetradentate ligand (L4) coordinating the ruthenium with two amino/imino groups and two thioether groups (i.e. ligand providing a coordination sphere of the type $N_2S_2$).

According to any one of the above embodiments of the invention, the ruthenium catalyst or pre-catalyst (also referred to from herein as complex) can be of the general formula

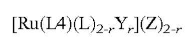

$$[Ru(L4)(L)_{2-r}Y_r](Z)_{2-r} \qquad (1)$$

wherein r represents 0, 1 or 2;

L4 represents one $C_{10-40}$ tetradentate ligand coordinating the Ru metal with:

- two nitrogen atoms, each in the form of a primary or secondary amine (i.e. a $NH_2$ or NH group) or N-alkyl imine functional groups (i.e. a C═N group), and two sulfur atoms, each in the form of thioether functional groups; and each L represents, simultaneously or independently, a neutral $C_1$-$C_{26}$ neutral monodentate ligand;

each Y represents, simultaneously or independently, a halogen atom, a hydrogen atom, a $BH_4$ group, a hydroxyl group, a $C_1$-$C_{10}$ alkoxyl group or an $C_3$-$C_{15}$ alkyl group;

each Z represents, simultaneously or independently, $ClO_4^-$, $BF_4^-$, $PF_6^-$, $SbCl_6^-$, $AsCl_6^-$, $SbF_6^-$, $AsF_6^-$, a $R^dSO_3^-$ wherein $R^d$ is a chlorine of fluoride atom or an $C_1$-$C_8$ alkyl, aryl, fluoroalkyl or fluoroaryl group, or a $BR^e{}_4^-$ wherein $R^e$ is a phenyl group optionally substituted by one to five groups such as halide atoms and/or methyl and/or $CF_3$ groups.

In a particular embodiment of formula (1), each Y represents, simultaneously or independently, a hydrogen atom, a hydroxyl, a $C_1$ to $C_{10}$ alkoxyl group, such as a methoxyl, ethoxyl or isopropoxyl group, or a $C_3$-$C_6$ alkyl group, such as allyl (i.e. propenyl), 2-methyl-allyl (i.e. 2-methyl-propenyl).

According to any one of the above embodiments of formula (1), each Z represents, simultaneously or independently, $ClO_4^-$, $BF_4^-$, $PF_6^-$, $SbCl_6^-$, $AsCl_6^-$, $SbF_6^-$, $AsF_6^-$, a $R^dSO_3^-$ wherein $R^d$ is a chlorine of fluoride atom or a $CF_3$ group, or a $BR^e{}_4^-$ wherein $R^e$ is a phenyl group optionally substituted by one, two or three groups such as halide atoms and/or methyl and/or $CF_3$ groups.

According to any one of the above embodiments of formula (1), the monodentate ligand L can be a $C_{3-24}$ monophosphine, like $PPh_3$, CO (carbon monoxide) or even, and preferably, a solvent. By the term "solvent" it has to be understood the usual meaning in the art and in particular compounds used as diluents in the preparation of the complex or during the invention's process. Non limiting examples of such solvent are acetonitrile, an alcohol (e.g. an $C_1$-$C_4$ alcohol), water, an ether (e.g. THF or diethylether), pyridine, a $C_3$-$C_8$ ester, or the substrate of the invention's process.

According to any one of the above embodiments of formula (1), it can be used as complex a compound of formula (1) wherein r is 2, i.e. of formula $$[Ru(L4)Y_2] \quad (1')$$

wherein L4 and Y have the meaning indicated above.

The complexes of the invention can be added into the reaction medium of the invention's process in a large range of concentrations. As non-limiting examples, one can cite as complex concentration values those ranging from 10 ppm to 50000 ppm, relative to the amount of substrate. Preferably, the complex concentration will be comprised between 100 and 10000, or even 1000, ppm. It goes without saying that the optimum concentration of complex will depend, as the person skilled in the art knows, on the nature of the latter, on the nature of the substrate and on the pressure of $H_2$ used during the process, as well as the desired time and temperature of reaction.

The hydrogenation process of the invention is carried out in the presence of a base. Said base can be the substrate itself, if the latter is basic, a corresponding alkoxide or any organic or inorganic base having preferentially a $pK_a$ above 10.

From the definition of formula (I) and in particular of its anion Y, it is evident that the base may also be provided by the complex itself (e.g. Y is hydrogen or a OH or alkoxyl group or a methylallyl). In such case, the base is considered as being present in the process in up to two molar equivalents compared to the Ru complex.

However, in any case it is in general beneficial to add an additional amount of base, especially if working with low catalyst amounts.

According to a particular embodiment of the invention, said base may have a $pK_a$ above 14. It is also understood that preferably said base does not reduce by itself a substrate of formula (I). As non-limiting examples one may cite the following types of base: an aluminum or boron hydride, an alkaline or alkaline-earth metal hydroxide, or an alkoxide of formula $(R^{31}O)_2M$ or $R^{31}OM'$, wherein M is an alkaline-earth metal, M' is an alkaline metal or an ammonium $NR^{32}{}_4^+$, $R^{31}$ stands for hydrogen or a $C_1$ to $C_8$ hydrocarbon group and $R^{32}$ stands for a $C_1$ to $C_{10}$ linear or branched alkyl group, such as sodium or potassium alkoxides. Of course, other suitable bases can be used.

According to an embodiment of the invention, said base is a $C_{1-8}$ alkoxide, alkaline or alkaline-earth hydroxides, such as sodium, potassium or calcium hydroxide, or inorganic hydrides such as $NaBH_4$, NaH or KH.

Useful quantities of base, added to the reaction mixture, may be comprised in a relatively large range. From the definition of formula (1) and of the base, it is evident that said base can be also comprised or incorporated in the catalyst itself. However, it is always beneficial to add an additional amount of base especially if working with a low catalyst load. One can cite, as non-limiting examples, ranges between 1 to 50000 molar equivalents, relative to the complex (e.g. base/com=up to 50000), preferably 1 to 2000, and even more preferably between 1 and 100 molar equivalents.

The hydrogenation reaction can be carried out in the presence or absence of a solvent. In a particular embodiment of the invention, the process is carried out in the presence of a solvent (in general for practical reasons), and any solvent current in hydrogenation reactions can be used for the purposes of the invention. Non-limiting examples include $C_{2-5}$ nitril alkyl such as acetonitril, $C_{3-8}$ N,N-dialkyl amide such as dimethyl formamide, $C_{3-9}$ ethers such as tetrahydrofuran or MTBE, polar solvents such as dimethyl sulfoxide or $C_{1-5}$ primary or secondary alcohols such as isopropanol or ethanol, or mixtures thereof. In particular said solvent can be selected amongst $C_{1-5}$ primary or secondary alcohols such as methanol, isopropanol or ethanol, or mixtures thereof or mixtures of said alcohols with the other herein above mentioned solvents.

The choice of the solvent is a function of the nature of the complex and the person skilled in the art is well able to select the solvent most convenient in each case to optimize the hydrogenation reaction.

In the hydrogenation process of the invention, the reaction can be carried out at a $H_2$ pressure comprised between $10^5$ Pa and $80\times10^5$ Pa (1 to 80 bars) or even more if desired. Again, a person skilled in the art is well able to adjust the pressure as a function of the catalyst load and of the dilution of the substrate in the solvent. As examples, one can cite typical pressures of 10 to $50\times10^5$ Pa (1 to 50 bar).

The temperature at which the hydrogenation can be carried out is comprised between 0° C. and 120° C., preferably in the range of between 20° C. and 100° C. Of course, a person skilled in the art is also able to select the preferred temperature as a function of the melting and boiling point of the starting and final products as well as the desired time of reaction or conversion.

According to any one of the above embodiments of formula (1), L4 can be a compound of formula

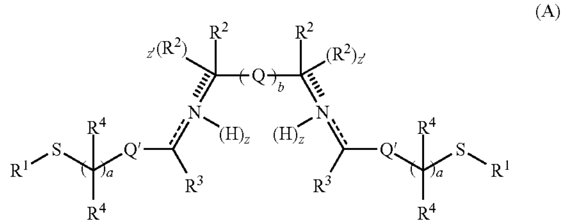

wherein a is 0 or 1, b is 0 or 1;

each z and z' is 1, in which case the all dotted and hatched lines represent a single bond (amino group); or z' is 1 and z is 0, in which case the all hatched lines represent a single bond and all dotted lines represent a double bond (imino group); or z' is 0 and z is 1, in which case the all dotted lines represent a single bond and all hatched lines represent a double bond (imino group); and each $R^1$ represents a linear, branched or cyclic $C_1$ to $C_{12}$ alkyl or alkenyl group optionally substituted or an $C_{6-10}$ aromatic group optionally substituted; and each $R^2$ represents a hydrogen atom, a $C_{1-10}$ alkyl or alkenyl group optionally substituted or a $C_{6-10}$ aromatic group optionally substituted; two adjacent $R^2$, taken together, may form a saturated or unsaturated cycle containing 5 to 12 atoms and including the atoms to which said $R^2$ are bonded, and being optionally substituted;

each $R^3$ represents a hydrogen atom or a $C_{1-10}$ alkyl or alkenyl group optionally substituted or a $C_{6-10}$ aromatic group optionally substituted;

each $R^4$ represents a hydrogen atom, a $C_{1-10}$ alkyl or alkenyl group optionally substituted or a $C_{6-10}$ aromatic group optionally substituted;

each Q' represents a $C_{10}$-$C_{16}$ metallocenediyl, a diphen-2,2'-yl, a 1,1'-binaphthalene-2,2'-diyl, a benzene-1,2-diyl, a naphthalenediyl group optionally substituted; and Q represents a Q' group or a group of formula

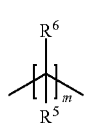

wherein m is 1 or 2 and each $R^5$ and $R^6$ represent, simultaneously or independently, a hydrogen atom, a $C_{1-10}$ alkyl or alkenyl group optionally substituted, a $C_{6-10}$ aromatic group optionally substituted; two distinct $R^6$ and/or $R^5$ groups, taken together, may form a $C_{3-8}$, or even up to $C_{10}$, saturated, unsaturated or aromatic ring optionally substituted, including the atoms to which said $R^6$ and/or $R^5$ groups are bonded.

Non-limiting examples of possible substituents of said $R^1$, $R^2$, $R^3$, $R^4$, $R^5$, $R^6$ or Q' are one, two, three or four groups selected amongst i) halogen atom (in particular when said substituents are on aromatic moieties), ii) $C_{5-12}$ cycloalkyl or cycloalkenyl, iii) $C_{1-10}$ alkoxy, alkyl, alkenyl, polyalkyleneglycols or halo- or perhalo-hydrocarbon, iv) a benzyl group or a fused or non-fused phenyl or indanyl group, said group being optionally substituted by one, two or three halogen, $C_{1-8}$ alkyl, alkoxy, or halo- or perhalo-hydrocarbon groups. The Q' group may also be substituted by one or two amino, nitro or sulfonate groups or by one or two groups of formula O—$(CR^8{}_2)_n$—O or O—$(CR^8{}_2)_n$—$NR^7$ wherein n is 1 or 2 and $R^8$ being a hydrogen atom or a $C_{1-4}$ alkyl group. The expression "halo- or perhalo-hydrocarbon" has here the usual meaning in the art, e.g. groups such as $CF_3$ or $CClH_2$ for instance.

As mentioned above, in said ligand (A) the atoms which may coordinate the Ru atom are the N atom and the S atom.

For the sake of clarity, and as mentioned above, in any one of the embodiments of the present invention, whenever two groups of formula (A) are taken together to form a cycle or ring said cycle or ring can be a mono or bi-cyclic group.

The ligand of formula (A) can be in a racemic or optically active form.

According to any one of the above embodiments of the ligand L4, said ligand is one wherein a is 0 and b is 0 or 1.

According to any one of the above embodiments of the ligand L4, each $R^1$ represents, a linear, branched or cyclic $C_1$ to $C_{10}$ alkyl or alkenyl group optionally substituted or a $C_{6-10}$ aromatic group optionally substituted.

According to any one of the above embodiments of the ligand L4, each $R^2$ represents a hydrogen atom, a $C_{1-6}$ alkyl or alkenyl group optionally substituted or a $C_{6-10}$ aromatic group optionally substituted; two adjacent $R^2$, taken together, may form a saturated or unsaturated cycle containing 5 to 8 atoms and including the atoms to which said $R^2$ are bonded, and being optionally substituted.

According to any one of the above embodiments of the ligand L4, each $R^3$ represents a hydrogen atom or a $C_{1-6}$ alkyl or alkenyl group optionally substituted or a $C_{6-10}$ aromatic group optionally substituted.

According to any one of the above embodiments of the ligand L4, each $R^4$ represents a hydrogen atom, a $C_{1-6}$ alkyl or alkenyl group optionally substituted or a $C_{6-10}$ aromatic group optionally substituted.

According to any one of the above embodiments of the ligand L4, Q represents a Q' group or a group of formula

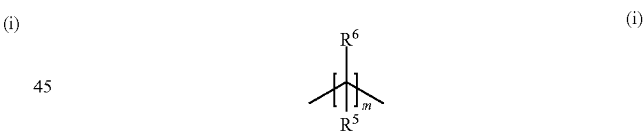

wherein m is 1 and $R^5$ and $R^6$ represent, simultaneously or independently, a hydrogen atom, a $C_{1-6}$ alkyl or alkenyl group optionally substituted, or a phenyl group optionally substituted; two distinct $R^6$ and/or $R^5$ groups, taken together, may form a $C_{3-6}$ saturated or unsaturated ring optionally substituted, including the atoms to which said $R^6$ and/or $R^5$ groups are bonded.

According to any one of the above embodiments of the ligand L4, the possible substituents of said $R^1$, $R^2$, $R^3$, $R^4$, $R^5$, $R^6$ or Q' are one, two or three groups selected amongst i) halogen atom (in particular when said substituents are on aromatic moieties), ii) $C_{5-6}$ cycloalkyl or cycloalkenyl, iii) $C_{1-6}$ alkoxy, alkyl or halo- or perhalo-hydrocarbon, iv) a benzyl group or a fused or non-fused phenyl or indanyl group, said group being optionally substituted by one, two or three halogen, $C_{1-4}$ alkyl or alkoxy groups.

According to any one of the above embodiments of the ligand L4, said ligand can be a compound of formula (B)

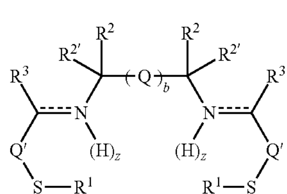

wherein b is 0 or 1;

each z is 1, in which case the all dotted lines represent a single bond (amino group); or z is 0, in which case the all dotted lines represent a double bond (imino group); and each $R^1$ represents, a linear, branched or cyclic $C_1$ to $C_{10}$ alkyl group optionally substituted or a $C_{6-10}$ aromatic group optionally substituted; and each $R^2$ or $R^{2'}$ represents a hydrogen atom, a $C_{1-6}$ alkyl or alkenyl group optionally substituted or a $C_{6-10}$ aromatic group optionally substituted; two adjacent $R^2$, or $R^2$ and $R^{2'}$, taken together, may form a saturated or unsaturated cycle containing 5 to 6 atoms and including the atoms to which said $R^2$ or $R^{2'}$ are bonded, and being optionally substituted;

each $R^3$ represents a hydrogen atom or a $C_{1-6}$ alkyl group optionally substituted; each Q' represents a 2,2'-diphenyl, a 1,1'-binaphthalene-2,2'-diyl, a benzene-1,2-diyl, a naphthalene-1,2-diyl or a naphthalene-2,3-diyl group optionally substituted; and Q represents a Q' group or a group of formula (i)

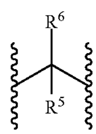

wherein $R^5$ and $R^6$ represent, simultaneously or independently, a hydrogen atom, a $C_{1-6}$ alkyl or alkenyl group optionally substituted, or a phenyl group optionally substituted; two distinct $R^6$ and/or $R^5$ groups, taken together, may form a $C_{3-6}$ saturated or unsaturated ring optionally substituted, including the atoms to which said $R^6$ and/or $R^5$ groups are bonded.

Possible substituents of said $R^1$, $R^2$, $R^{2'}$, $R^3$, $R^5$, $R^6$ or Q', in formula (B), are one, two or three groups selected amongst i) halogen atom (in particular when said substituents are on aromatic moieties), ii) $C_{5-6}$ cycloalkyl or cycloalkenyl, iii) $C_{1-6}$ alkoxy, alkyl or perhalo-hydrocarbon, iv) a benzyl group or a fused or non-fused phenyl or indanyl group, said group being optionally substituted by one, two or three halogen, $C_{1-4}$ alkyl or alkoxy, groups.

According to any one of the above embodiments of L4, possible substituents of said $R^1$, $R^2$, $R^{2'}$, $R^3$, $R^5$, $R^6$ Q or Q' are one, two or three groups selected amongst i) halogen atom (in particular when said substituents are on aromatic moieties), ii) $C_{5-6}$ cycloalkyl or cycloalkenyl, iii) $C_{1-4}$ or $C_{1-6}$ alkoxy, alkyl or perhalo-hydrocarbon, iv) a fused or non-fused phenyl group being optionally substituted by one, two or three halogen, $C_{1-4}$ alkyl or alkoxy, groups.

According to any one of the above embodiments of formula (B), said ligand is one wherein b is 0.

According to any one of the above embodiments of L4, said ligand can be a compound of formula (C)

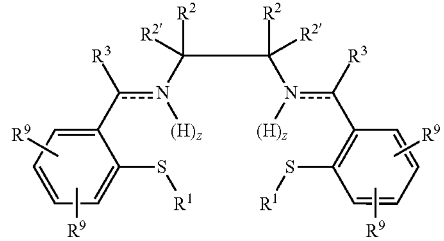

wherein each z is 1, in which case the all dotted lines represent a single bond (amino group); or z is 0, in which case the all dotted lines represent a double bond (imino group); and each $R^1$ represents, a linear, branched or cyclic $C_1$ to $C_{10}$ alkyl group optionally substituted or a $C_{6-10}$ aromatic group optionally substituted; and each $R^2$ or $R^{2'}$ represents a hydrogen atom, a $C_{1-6}$ alkyl or alkenyl group optionally substituted or a $C_{6-10}$ phenyl group optionally substituted; two adjacent $R^2$, or $R^2$ and $R^{2'}$, taken together, may form a saturated or unsaturated cycle containing 5 to 6 atoms and including the atoms to which said $R^2$ or $R^{2'}$ are bonded, and being optionally substituted;

each $R^3$ represents a hydrogen atom or a $C_{1-6}$ alkyl group optionally substituted; and each $R^9$ represents a hydrogen atom, a halogen atom, such as Cl or F, a $C_{1-6}$ alkoxy, alkyl or perhalo-hydrocarbon, or a benzyl or phenyl group optionally substituted; or two adjacent $R^9$ bonded to the same benzene ring, taken together, represents a fused phenyl or indanyl group, said group being optionally substituted by one, two or three halogen, $C_{1-4}$ alkyl or alkoxy groups.

Possible substituents of said $R^1$, $R^2$, $R^{2'}$, $R^3$ or $R^9$, in formula (C), are one or two groups selected amongst i) halogen atom (in particular when said substituents are on aromatic moieties), ii) $C_{1-6}$ alkoxy, alkyl or perhalo-hydrocarbon.

According to a particular embodiment or formula (C), each $R^9$ represents a hydrogen atom, a halogen atom, such as Cl or F, a $C_{1-4}$ alkoxy, alkyl or perhalo-hydrocarbon, or a phenyl group optionally substituted; or two adjacent $R^9$ bonded to the same benzene ring, taken together, represents a fused phenyl group, said group being optionally substituted by one, two or three halogen, $C_{1-4}$ alkyl or alkoxy groups.

According to any one of the above embodiments of L4, each $R^3$ represents a hydrogen atom.

According to any one of the above embodiments of formula (B) or (C), each $R^{2'}$ represents a hydrogen atom, a $C_{1-4}$ alkyl group or phenyl group optionally substituted as above mentioned.

According to any one of the above embodiments of L4, each $R^2$ represents a hydrogen atom, a $C_{1-4}$ alkyl group or phenyl group optionally substituted as above mentioned; or two adjacent $R^2$, taken together, may form a saturated cycle containing 5 to 6 atoms and including the atoms to which said $R^2$ or $R^{2'}$ are bonded, and being optionally substituted as above mentioned. In particular each $R^2$ may represent a hydrogen atom, a $C_{1-4}$ alkyl group or phenyl group optionally substituted as above mentioned; or two adjacent $R^2$, taken together, may form a cyclohexyl group including the atoms to which said $R^2$ or $R^{2'}$ are bonded.

According to any one of the above embodiments of L4, said $R^1$, $R^2$, $R^{2'}$, $R^3$ or $R^4$ are unsubstituted groups as defined above (i.e. the optionally substitution is not applicable).

According to any one of the above embodiments of L4, non-limiting examples of such alkyl group may be a Me, $^i$Pr, $^t$Bu, $^i$Bu, $^s$Bu, $^n$Pentyl cyclopentyl, cylohexyl or adamantly group.

According to any one of the above embodiments of L4, non-limiting examples of aromatic group optionally substituted are indanyl, $C_6H_5$ (phenyl), $C_{10}H_7$ (naphthyl), $(X)_rC_6H_{5-r}$, or $(X)_rC_{10}H_{7-r}$, r being 1 or 2 and X being F, Cl, $CF_3$, $(X)_rC_6H_{5-r}$, or a $C_{1-4}$ alkoxy, sulfide or alkyl group (such as $^t$Bu or OMe or Me).

According to any one of the above embodiments of L4, $R^1$ is a group as exemplified herein above for alkyl or aromatic groups.

According to any one of the above embodiments of L4, non-limiting examples of Q' are $C_6H_4$ (benzene-1,2-diyl), $C_{10}H_6$ (naphthalene-1,2-diyl or a naphthalene-2,3-diyl), $(X)_rC_6H_{4-r}$, or $(X)_rC_{10}H_{6-r}$, r being 1 or 2 and X being F, Cl, $CF_3$, $(X)_vC_6H_{5-v}$ or a $C_{1-4}$ alkoxy or alkyl group (such as $^t$Bu or OMe or Me).

According to any one of the above embodiments of L4, Q is a group of formula (i) and non-limiting examples of said Q are $CH_2$, $CMe_2$ or $CH_2CH_2$.

According to any one of the above embodiments of L4, by "aromatic group or ring" it is meant a phenyl or naphthyl group, and in particular a phenyl group.

According to any one of the above embodiments of L4, said ligand is one wherein all the dotted lines represent a double bond (imino group) and at least one $R^1$ group is an alkyl group.

According to any one of the above embodiments of L4, said ligand is one wherein the all dotted lines represent a single bond (amino group).

According to any one of the above embodiments of L4, said $R^3$ is a hydrogen atom.

For the sake of clarity, in the present application by the expression "lines represent a single/double bond", or the similar, it is meant the normal meaning understood by a person skilled in the art, i.e. that the whole bonding (solid and dotted/hatched line) between the atoms connected by said lines is a single or double bond.

As non limiting examples of L4 ligands one can cite the following ones:

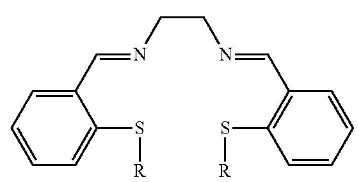

R = Me I
iPr II
Cyclohexyl III
tBu IV

-continued

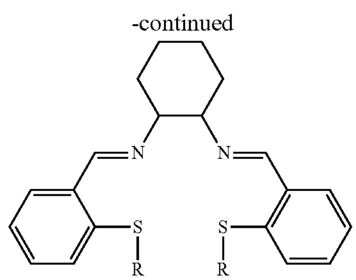

R = Me V
iPr VI
Cyclohexyl VII
tBu VIII
1-Adamantyl IX
Ph X
2,6-$Me_2$—$C_6H_3$ XI
1-Naphthyl XII
4-tBu—$C_6H_4$ XIII
4-F—$C_6H_4$ XIV

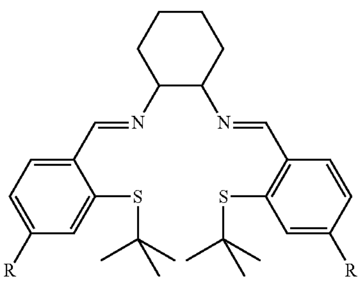

R = $CF_3$ XV
Br XVI
Ph XVII
tBu XVIII

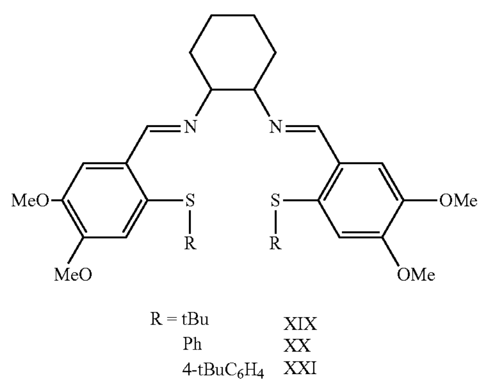

R = tBu XIX
Ph XX
4-tBu$C_6H_4$ XXI

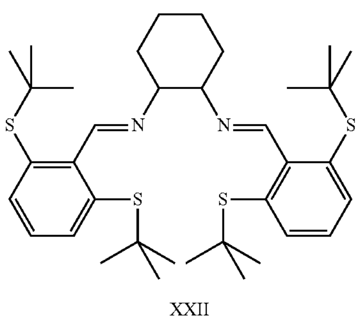

XXII

-continued

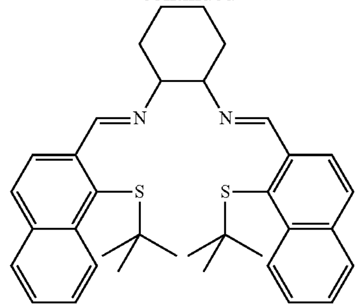

XXIII

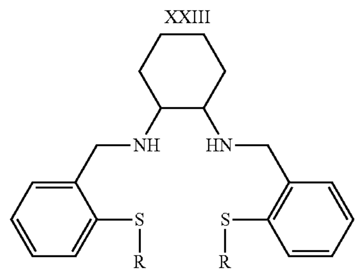

| R = | |
|---|---|
| Cyclohexyl | XXIV |
| tBu | XXV |
| Ph | XXVI |
| 1-Naphthyl | XXVII |
| 2,6-$Me_2$—$C_6H_3$ | XXVIII |
| 4-tBu—$C_6H_3$ | XXIX |
| 4-F—$C_6H_3$ | XXX |

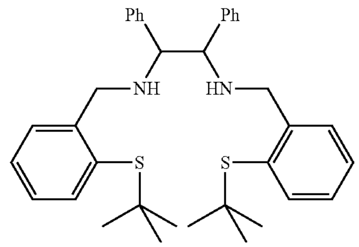

XXXI

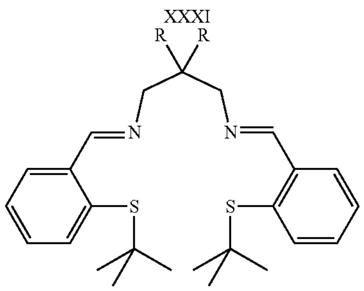

| R = | |
|---|---|
| H | XXXII |
| Me | XXXIII |

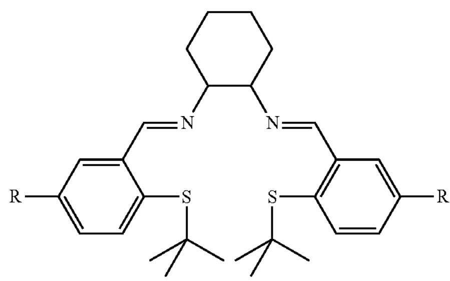

| R = | |
|---|---|
| $NO_2$ | XXXIV |
| $NMe_2$ | XXXV |

-continued

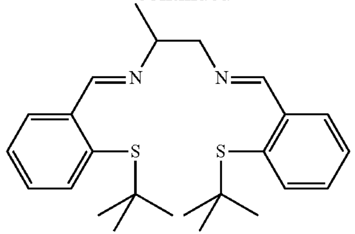

XXXVI said compounds I to XXXVI being in an optically active form or in a racemic form, if applicable.

The ligands (A), (B) or (C) described above, wherein both dotted lines represent each a single bond and b is 0, are also an object of the present invention since are novel compounds, at the exception of ligands N,N'-bis(2-(hexylthio)benzyl) ethane-1,2-diamine disclosed by D. Scott Bohle et al. in *Inorg. Chem.,* 2000, 39, 712 and N-(2-(benzylthio)benzyl)-N'-(2-(tert-butylthio)benzyl)ethane-1,2-diamine disclosed by D. A. Nation in *J. Chem. Soc. Dalton Trans.,* 1996, 3001, both ligands are described for their coordination chemistry.

The invention's ligands can be obtained by applying standard general methods which are well known in the state of the art and by the person skilled in the art. In particular said ligands can be prepared as described in the Examples.

The complexes of formula (1) or (1'), as above described, are also another object of the invention since are new compounds, at the exception of complex $RuCl_2$(IV) (N,N'-bis(2-(tert-butylthio-κS)benzylidene)-1,2-ethanediamino-κN,κN') dichlororuthenium(II)), $RuCl_2$(VIII) ((N,N'-bis(2-(tert-butylthio-κS)benzylidene)-1,2-cyclohexyldiamino-κN,κN') dichlororuthenium(II)), $RuCl_2$(XXXII) (N,N'-bis(2-(tert-butylthio-κS)benzylidene)-1,3-propanediamino-κN,κN') dichlororuthenium(II)) and $RuCl_2$(XXXVI) N,N'-bis(2-(tert-butylthio-κS)benzylidene)-1,2-propanediamino-κN,κN') dichlororuthenium(II) described in Nakajima, K., Ando, Y., Mano, H., Kojima, M., *Inorg. Chim. Acta* 1998, 274 184 for their crystal structures and electrochemical properties.

The complex (1) of the invention can be used in the form of a preformed complex or can be generated in situ, in the reaction medium of the hydrogenation.

In any case, according to a particular embodiment of the invention, the catalyst or pre-catalyst is obtained or obtainable by a process comprising reacting together:

1) a ruthenium precursor of formula $$[Ru(\text{“diene”})(L')_vE_{2-v}] \quad (2)$$

wherein v represents 0, 1 or 2;

E represents a mono anion;

"diene" represents a linear or branched $C_4$-$C_{15}$ hydrocarbon group comprising two carbon-carbon double bonds, optionally substituted, or a cyclic $C_7$-$C_{20}$ hydrocarbon group comprising two carbon-carbon double bonds, optionally substituted; and L' represents a $C_3$-$C_{15}$ alkyl, a $C_6$-$C_{12}$ aromatic ring optionally substituted or a $C_7$-$C_{15}$ triene;

2) with a ligand L4, defined as above; and 3) with optionally between approximately 0.5 and 5 molar equivalent of base.

Optional substituent of the "diene" or of L' are one or two $C_1$-$C_{10}$ alkyl or aryl groups, $C_1$-$C_6$ alkoxy groups or —C(O)O—($C_1$-$C_6$ alkyl) groups.

It is understood that "allyl" possesses the usual meaning in the art, i.e. a group comprising a fragment C═C—$C^-$, or C═C—C●. Similarly, it is understood that "triene" possesses the usual meaning in the art, i.e. a group comprising three non aromatic carbon-carbon double bonds.

According to a particular embodiment of the invention, E represents a mono anion selected amongst the group consisting of halides (e.g. Cl, Br, I,), $BF_r^-$, $ClO_4^-$, $PF_6^-$, $SbCl_6^-$, $AsCl_6^-$, $SbF_6^-$, $AsF_6^-$, hydroxylate, $C_1$-$C_{10}$ carboxylates (e.g. acetate, proprionate, 2-Et-hexanoate), a $C_5$-$C_{10}$ 1,3-diketonate, $R^iSO_3^-$ wherein $R^1$ is a chlorine of fluoride atom or a $C_1$-$C_8$ alkyl, aryl, fluoroalkyl or fluoroaryl group, or $BR^j_4{}^-$ wherein $R^j$ is a phenyl group optionally substituted by one to five groups such as halide atoms or methyl or $CF_3$ groups.

As non-limiting examples of suitable ruthenium precursors one can cite the compound (2) wherein "diene" stands for a $C_7$-$C_{10}$, hydrocarbon group comprising two carbon-carbon double bonds, such as for example COD (cycloocta-1,5-diene) or NBD (norbornadiene), or yet cyclohepta-1,4-diene.

As non-limiting examples of suitable ruthenium precursors, one can cite the compound (2) wherein "allyl" stands for a $C_3$-$C_{10}$, or even $C_3$-$C_6$, hydrocarbon group comprising a fragment C═C—C⁻, or C═C—C●, such as for example allyl or 2-methyl-allyl (see, for instance, J. Powell et al., in J. Chem. Soc., (A), 1968, 159; M. O. Albers et al., Inorganic Synth., 1989, 26, 249; R. R. Schrock et al., J. Chem. Soc. Dalton Trans., 1974, 951).

As non-limiting examples of suitable ruthenium precursors, one can cite the compound (2) wherein "aromatic ring" stands for a $C_6$-$C_{12}$ group comprising a benzene ring, such as an indane or a p-cymene such as for example benzene, para-cymene (6-isopropyl-toluene) or hexamethyl benzene.

As non-limiting examples of suitable ruthenium precursors, one can cite the compound (2) wherein "triene" stands for a $C_7$-$C_{10}$ hydrocarbon group comprising three non aromatic carbon-carbon double bonds, such as for example COT (cyclooctatriene).

The preparation of the catalyst may benefit from the presence of a base, in particular when in compound (2) E represents a halogen or a carboxylate group. Said base can be defined as for the base of the hydrogenation process described herein above.

As specific, but non limiting, examples of said ruthenium precursor (2), one may cite the following:

[Ru("diene")("allyl")$_2$] such as [Ru(COD)(2-methallyl)$_2$], [Ru(COD)(allyl)$_2$], [Ru(NBD)(2-methallyl)$_2$] or [Ru(NBD)(allyl)$_2$];

[Ru("diene")E$_2$] such as [Ru(COD)(Cl)$_2$] or [Ru(NBD)(Cl)$_2$];

[Ru("diene")("triene")] such as [Ru(COD)(COT)]; or

[Ru("diene") ("arene")] such as [Ru(COD)($C_6H_6$)], [Ru($C_6H_6$)(cyclohexadiene)], [Ru(COD)($C_8H_8$)], [Ru(COD)(1,4-$C_6H_4Me_2$)] or [Ru(COD)(1,3,5-$C_6H_3Me_3$)].

The preparation of the catalyst/pre-catalyst can be carried out in a suitable solvent. Said solvent could be the substrate of the hydrogenation processes itself or another one. Typically there is used the same solvent as for the subsequent hydrogenation as described herein above. Typical non-limiting examples are given herein below, when describing the hydrogenation process.

A typical example of such procedure to prepare the invention's catalysts is provided in the examples.

EXAMPLES

The invention will now be described in further detail by way of the following examples, wherein the temperatures are indicated in degrees centigrade and the abbreviations have the usual meaning in the art.

All the procedures described hereafter have been carried out under an inert atmosphere unless stated otherwise. Hydrogenations were carried out in a stainless steel autoclave. $H_2$ gas (99.99990%) was used as received. All substrates were distilled from appropriate drying agents or filtered through basic alumina. All solvents were reagent-grade and used without any prior distillation. NMR spectra were recorded on a Bruker AM-400 ($^1$H at 400.1 MHz, $^{13}$C at 100.6 MHz, and $^{31}$P at 161.9 MHz) spectrometer and normally measured at 300 K, in $CDCl_3$ unless indicated otherwise. Chemical shifts are listed in ppm from TMS as internal standard.

The following ketones and aldehydes from A to Y are the substrates used in examples 1 to 57:

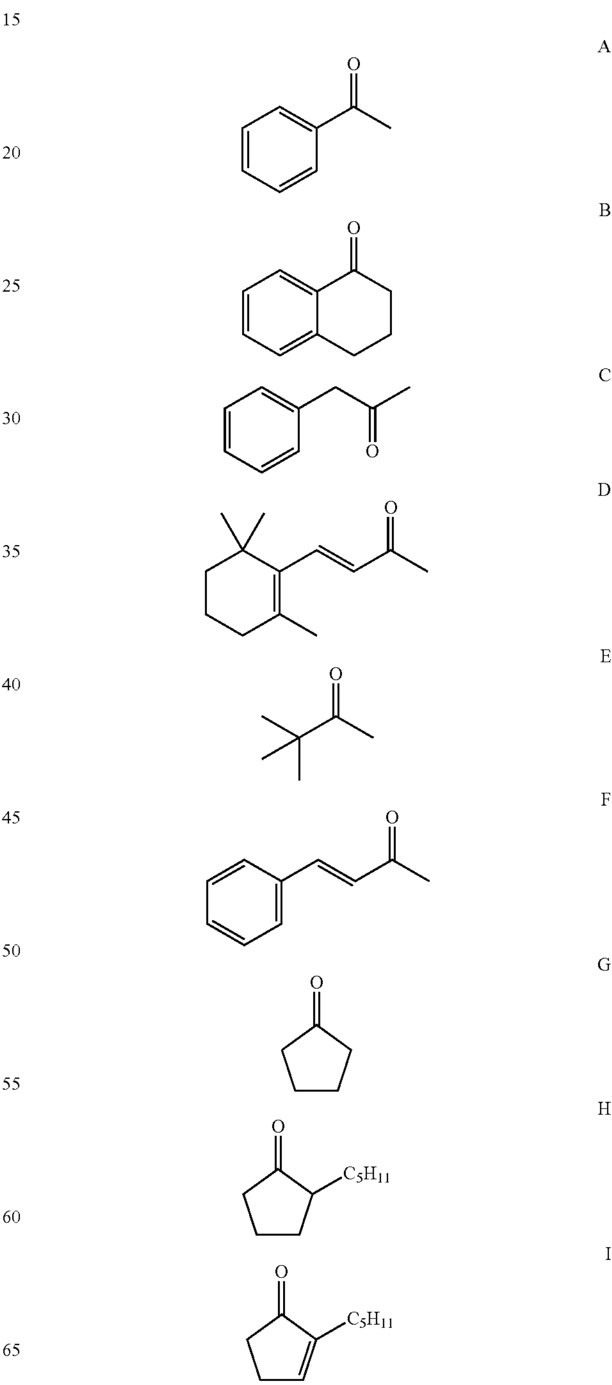

-continued

J

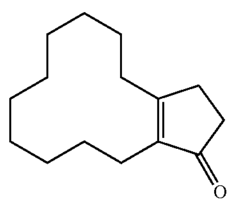

K

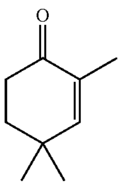

L

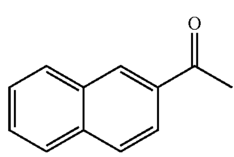

M

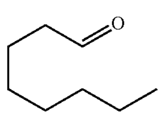

N

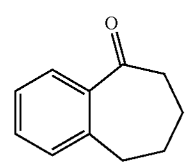

O

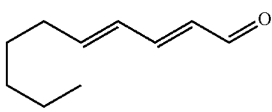

P

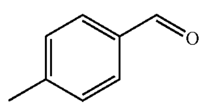

Q

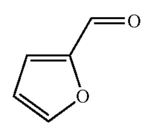

R

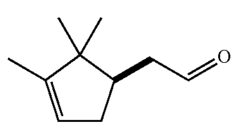

S

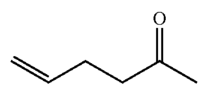

T

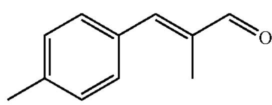

-continued

U

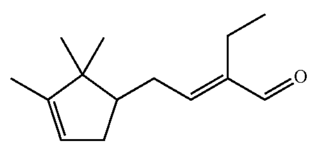

V

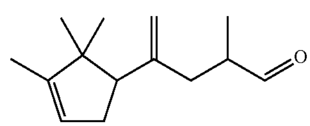

W

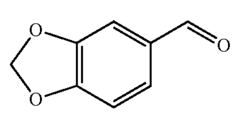

X

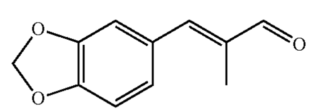

Y

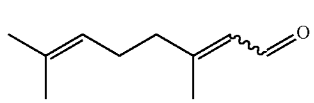

Z

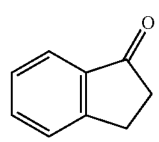

Examples 1-23

Catalytic Hydrogenation of Ketone A Using Various Invention's Ruthenium Complexes The hydrogenation substrate A (20 mmol), the catalyst precursor $RuCl_2(L4)$ (0.01 mmol), the base, and iso-propanol (10 ml) were placed in a pressure reactor and stirred under hydrogen (50 bar) at the temperature and for the period indicated in Table 1.

TABLE 1

| Example No. | L4 | Base | Temp (° C.) | Reaction time | Conv. (%) | ee (%) |
|---|---|---|---|---|---|---|
| 1 | I | KOH (0.1 mmol) | 60 | 16 h | 99 | — |
| 2 | II | KOH (0.1 mmol) | 60 | 2 h | 99 | — |
| 3 | IV | tBuOK (0.1 mmol) | 60 | 0.5 h | 99 | — |
| 4 | V | tBuOK (0.1 mmol) | 60 | 1.5 h | 99 | 44 |
| 5 | VI | KOH (0.1 mmol) | 60 | 2 h | 99 | 50 |
| 6 | VII | tBuOK (0.1 mmol) | 60 | 2 h | 99 | 33 |
| 7 | VIII | tBuOK (0.1 mmol) | 60 | 0.5 h | 99 | 71 |
| 8 | VIII | tBuOK (0.1 mmol | 23 | 1 h | 99 | 77 |
| 9 | VIII | KOH (1 mmol) | 23 | 1.5 h | 96 | 81 |

TABLE 1-continued

| Example No. | L4 | Base | Temp (° C.) | Reaction time | Conv. (%) | ee (%) |
|---|---|---|---|---|---|---|
| 10* | VIII | LiOH (2 mmol) | 60 | 2 h | 99 | 61 |
| 11 | XV | KOH (0.1 mmol) | 80 | 4 h | 66 | 50 |
| 12 | XVI | KOH (1 mmol) | 45 | 1.5 h | 99 | 53 |
| 13 | XVII | KOH (1 mmol) | 23 | 5 h | 27 | 80 |
| 14 | XVIII | KOH (1 mmol) | 60 | 1 h | 99 | 83 |
| 15 | XIX | tBuOK (0.1 mmol) | 60 | 10 min | 99 | 64 |
| 16 | XXII | KOH (0.1 mmol) | 23 | 18 h | 99 | 77 |
| 17 | XXV | tBuOK (0.1 mmol) | 60 | 1 h | 99 | 69 |
| 18 | XXVI | tBuOK (0.1 mmol) | 60 | 20 min | 99 | 57 |
| 19 | XXVII | KOH (0.1 mmol) | 60 | 2 h | 91 | 17 |
| 20 | XXXII | KOH (0.1 mmol) | 60 | 3 h | 99 | — |
| 21 | XXXIV | KOH (0.1 mmol) | 60 | 1 h | 99 | 67 |
| 22 | XXXV | KOH (0.1 mmol) | 60 | 1.5 h | 99 | 58 |
| 23 | XXXVI | KOH (0.1 mmol) | 60 | 4 h | 99 | 30 |

*MeOH (10 ml) was used as solvent.

Examples 24-48

Catalytic Hydrogenation of Ketones or Aldehydes Using Various Invention's Ruthenium Complexes The hydrogenation substrate (20 mmol), the base (as in Table 2), iso-propanol (10 ml), and the catalyst precursor $RuCl_2(L4)$ (0.01 mmol) were placed into a pressure reactor and stirred under $H_2$ (50 bar) at the given temperature for the given amount of time as indicated in Table 2.

TABLE 2

| Example No. | Substrate | L4 | Base | Temp (° C.) | Reaction Time | GC Yield (%) | ee (%) |
|---|---|---|---|---|---|---|---|
| 24 | C | VIII | KOH (1 mmol) | 23 | 5 h | 99 | 30 |
| 25 | C | XVIII | KOH (0.1 mmol) | 60 | 2.5 h | 99 | 40 |
| 26 | D | VIII | NaOH (0.1 mmol) | 23 | 2 h | 96 | 62 |
| 27 | E | V | KOH (1 mmol) | 60 | 2.5 h | 30 | 57 |
| 28 | F | IV | tBuOK (0.1 mmol) | 60 | 3 h | 84 | — |
| 29 | F | VIII | tBuOK (0.1 mmol) | 60 | 3 h | 96 | 49 |
| 30 | G | IV | KOH (0.1 mmol) | 60 | 1.5 h | 99 | — |
| 31 | H | VIII | tBuOK (0.1 mmol) | 60 | 0.5 h | 99 | 26 (cis) (95:5 cis/trans) |
| 32 | H | XXV | tBuOK (0.1 mmol) | 60 | 1 h | 89 | 31 (cis) (97:3 cis/trans) |
| 33 | J | VIII | KOH (0.1 mmol) | 60 | 5 h | 54 | n.d. |
| 34 | L | VIII | KOH (0.1 mmol) | 60 | 2 h | 99 | 65 |
| 35 | L | XVIII | KOH (0.1 mmol) | 60 | 3 h | 99 | 83 |
| 36 | N | VIII | KOH (0.1 mmol) | 60 | 3 h | 99 | 35 |
| 37 | O | IV | KOH (0.1 mmol) | 60 | 5.5 h | 88 | — |
| 38 | P# | IV | KOH (4.25 mmol) | 60 | 2 h | 99* | — |
| 39 | Q | IV | KOH (0.1 mmol) | 60 | 3 h | 99 | — |
| 40 | R | IV | KOH (2 mmol) | 45 | 0.5 h | 99 | — |
| 41 | S | VIII | KOH (0.1mmol) | 60 | 2 h | 95 | n.d. |
| 42 | T‡ | IV | KOH (0.1 mmol) | 45 | 2 h | 99 | — |
| 43 | U† | IV | KOH (1 mmol) | 23 | 2 h | 94 | — |
| 44 | V† | IV | KOH (1 mmol) | 23 | 1.5 h | 98 | — |
| 45 | W | IV | tBuOK (0.1 mmol) | 60 | 2 h | 99 | — |
| 46 | X | IV | tBuOK (0.1 mmol) | 60 | 2 h | 99 | — |
| 47 | Y | IV | KOH (0.2 mmol) | 23 | 18 h | 52 | — |
| 48 | Z | VIII | tBuOK (0.1 mmol) | 60 | 2 h | 99 | 80 |

*30 ppm of $RuCl_2$(IV) as catalyst and methanol (8 ml) as solvent were used;
‡1.9 mmol
†MeOH (10 ml) was used as solvent;
85 mmol

Examples 49-60

Catalytic Hydrogenation of Ketones Using In-Situ Generated Various Invention's Ruthenium Complexes without External Base The ruthenium precursor [Ru(COD)(2-Methylallyl)$_2$] (0.02 mmol), the ligand L4 (0.02 mmol), and isopropanol (1 ml) were placed in a vial and stirred under argon at 60° C. for 1 h. This solution was added to a solution of substrate (20 mmol) and isopropanol (9 ml) in a pressure reactor and the mixture was stirred at 60° C. under hydrogen (50 bar) for the period of time as indicated in Table 3.

In these examples the base is the anion of the catalyst.

TABLE 3

| Example No. | Substrate | L4 | Time | Conv. (%) | ee (%) |
|---|---|---|---|---|---|
| 49 | A | V | 16 h | 63 | 38 |
| 50 | A | VII | 2 h | 99 | 57 |
| 51 | A | VIII | 2 h | 99 | 63 |
| 52 | A | IX | 2 h | 99 | 47 |
| 53 | A | X | 16 h | 36 | 39 |
| 54 | A | XIX | 2 h | 99 | 54 |
| 55 | A | XXVIII | 2 h | 99 | 76 |
| 56 | D | IX | 2 h | 80 | 62 |
| 57 | B | IX | 2 h | 99 | 86 |
| 58 | I | XXVIII | 2 h | 53 | n.d. |
| 59 | K | IX | 2 h | 89 | 82 |
| 60 | M | IV | 16 h | 26 | — |

Examples 61-64

Catalytic Hydrogenation of Ketones or Aldehydes Using In-Situ Generated Various Invention's Ruthenium Complexes and an External Base The ruthenium precursor [Ru(COD)Cl$_2$] (0.01 mmol), the ligand L4 (0.01 mmol), the base and a ketone or aldehyde were dissolved in isopropanol (10 ml) in a pressure reactor and stirred at 60° C. under hydrogen (50 bar) for the period of time as indicated in Table 4.

TABLE 4

| Example No. | Substrate | L4 | Base | Reaction time | Yield (%) | e.e. (%) |
|---|---|---|---|---|---|---|
| 61 | A | IV | tBuOK (0.1 mmol) | 2.5 h | 93 | — |
| 62 | A | VIII | tBuOK (0.1 mmol) | 2 h | 99 | 52 |
| 63 | A | XXXI | tBuOK (0.1 mmol) | 1.5 h | 99 | 60 |
| 64 | P | IV | KOH (0.1 mmol) | 2.5 h | 99 | — |

Synthesis of the Ligands

2-Thioetherbenzaldehyde General Procedure 2-nitrobenzaldehyde (33 mmol) and $K_2CO_3$ (37 mmol) were dissolved in dry DMF (50 ml) under a nitrogen atmosphere. The thiol (35 mmol) was then added at room temp. while stirring at a suitable rate to control the exothermic reaction and the mixture was stirred at 80° C. for 16 hour. The mixture was cooled at room temp., $H_2O$ (200 ml) was added and the mixture was extracted with MTBE/pentane (1:1). The organic layers were washed with aq. sat. $NH_4Cl$ solution and brine, dried with $MgSO_4$, and the solvents were distilled under reduced pressure. The crude product was purified by bulb-to-bulb distillation or column chromatography (Silica-gel, Pent/$Et_2O$).

2-(iso-Propylthio)benzaldehyde CAS: 53606-32-9

2-(Cyclohexylthio)benzaldehyde CAS: 503065-08-5

2-(Adamantan-1-ylthio)benzaldehyde

Yellow dense oil, 95% yield. $^1$H NMR (400 MHz, $CDCl_3$): δ 10.82 (s, 1H), 8.05-7.94 (m, 1H), 7.67-7.47 (m, 3H), 2.06-1.98 (m, 3H), 1.85-1.76 (m, 6H), 1.7-1.53 (m, 6H); $^{13}$C NMR (100 MHz, $CDCl_3$): δ 193.8 (CH), 140.3 (CH), 139.8 (C), 134.6 (C), 133.4 (CH), 129.5 (CH), 128.0 (CH), 49.7 (C), 43.7 ($CH_2$), 36.0 ($CH_2$), 30.0 (CH).

2-(Phenylthio)benzaldehyde CAS: 36943-39-2

2-((2,6-dimethylphenyl)thio)benzaldehyde CAS: 540774-00-3

2-(naphthalen-1-ylthio)benzaldehyde CAS: 866417-74-5

2-((4-(tert-butyl)phenyl)thio)benzaldehyde CAS: 643763-18-2

2-((4-fluorophenyl)thio)benzaldehyde CAS: 643763-14-8

2-(tert-butylthio)-4-(trifluoromethyl)benzaldehyde

Yellow oil, 87% yield. $^1$H NMR (400 MHz, $CD_2Cl_2$): δ 10.79 (d, $J_{HH}$=0.84 Hz, 1H), 8.1-8.05 (m, 1H), 7.94-7.89 (m, 1H), 7.82-7.74 (m, 1H), 1.31 (s, 9H); $^{13}$C NMR (100 MHz, $CD_2Cl_2$): δ 192.6 (CH), 142.5 (C), 142.5 (C), 138.1 (C), 137.0 (q, $T_{CF}$=3.7 Hz, CH), 134.9 (q, $T_{CF}$=32.8 Hz, C), 129.0 (CH), 126.6 (q, $T_{CF}$=3.7 Hz, CH), 123.8 (q, $J_{CF}$ 273.1 Hz, $CF_3$) 48.8 (C), 31.1 ($CH_3$); $^{19}$F NMR (376.5 MHz, $CD_2Cl_2$): δ-63.92 (s, 1F).

4-bromo-2-(tert-butylthio)benzaldehyde CAS: 1191415-77-6

3-(tert-butylthio)-[1,1'-biphenyl]-4-carbaldehyde

Pale red solid, 79% yield. $^1$H NMR (400 MHz, $CD_2Cl_2$): δ 10.79 (s, 1H), 8.06-8.01 (m, 1H), 7.90-7.87 (m, 1H), 7.79-7.73 (m, 1H), 7.69-7.64 (m, 2H), 7.52-7.47 (m, 2H), 7.46-7.42 (m, 1H), 1.34 (s, 9H); $^{13}$C NMR (100 MHz, $CD_2Cl_2$): δ 193.3 (CH), 146.6 (C), 139.5 (C), 138.8 (CH), 138.6 (C), 137.6 (C), 129.4 (CH), 129.0 (CH), 128.8 (CH), 128.5 (CH), 127.7 (CH), 48.0 (C), 31.2 ($CH_3$).

4-(tert-butyl)-2-(tert-butylthio)benzaldehyde

Yellow oil, 96% yield. $^1$H NMR (400 MHz, $CD_2Cl_2$): δ 10.71 (d, $J_{HH}$=0.84 Hz, 1H), 7.90 (d, $J_{HH}$=8.20 Hz, 1H), 7.65 (d, $J_{HH}$=2.00 Hz, 1H), 7.55 (ddd, $J_{HH}$=8.20 Hz, $J_{HH}$=2.00 Hz, $J_{HH}$=0.84 Hz, 1H), 1.36 (s, 9H), 1.28 (s, 9H); $^{13}$C NMR (100 MHz, $CD_2Cl_2$): δ 193.4 (CH), 157.9 (C), 137.7 (CH), 137.4 (C), 136.7 (C), 128.0 (CH), 127.1 (CH), 47.6 (C), 35.4 (C), 31.1 ($CH_3$), 31.1 ($CH_3$).

2-(tert-butylthio)-4,5-dimethoxybenzaldehyde

52% yield. $^1$H NMR (400 MHz, $CD_2Cl_2$): δ 10.61 (s, 1H), 7.51 (s, 1H), 7.06 (s, 1H), 3.97 (s, 3H), 3.96 (s, 3H), 1.32 (s, 9H); $^{13}$C NMR (100 MHz, $CDCl_3$): δ 192.5 (CH), 153.0 (C), 150.3 (C), 133.3 (C), 130.5 (C), 121.3 (CH), 109.5 (CH), 56.3 ($CH_3$), 56.1 ($CH_3$), 47.4 (C), 31.0 ($CH_3$).

4,5-dimethoxy-2-(phenylthio)benzaldehyde CAS: 213984-03-3

2-((4-(tert-butyl)phenyl)thio)-4,5-dimethoxybenzaldehyde

38% yield. $^1$H NMR (400 MHz, $CDCl_3$): δ10.44 (s, 1H), 7.46 (s, 1H), 7.35-7.29 (m, 2H), 7.2-7.14 (m, 2H), 6.86 (s, 1H), 3.95 (s, 3H), 3.83 (s, 3H), 1.28 (s, 9H); $^{13}$C NMR (100 MHz, $CDCl_3$): δ 190.6 (CH), 154.1 (C), 150.4 (C), 149.4 (C), 132.9 (C), 132.8 (C), 129.7 (C), 129.4 (CH), 126.5 (CH), 116.3 (CH), 110.5 (CH), 56.2 ($CH_3$), 34.5 (C), 31.2 ($CH_3$).

2,6-bis(tert-butylthio)benzaldehyde CAS: 918882-57-2

2-(tert-butylthio)-5-nitrobenzaldehyde

95% yield. $^1$H NMR (400 MHz, $CD_2Cl_2$): δ 10.69 (s, 1H), 8.70 (d, $J_{HH}$=2.7 Hz, 1H), 8.33 (dd, $J_{HH}$=8.5, 2.7 Hz, 1H), 7.84 (d, $J_{HH}$=8.5 Hz, 1H), 1.38 (s, 9H); $^{13}$C NMR (100 MHz, $CD_2Cl_2$): δ 191.3 (CH), 148.7 (C), 145.1 (C), 140.6 (CH), 140.4 (C), 127.2 (CH), 123.4 (CH), 49.8 (C), 31.2 ($CH_3$).

2-(tert-butylthio)-5-(dimethylamino)benzaldehyde

78% yield. $^1$H NMR (400 MHz, $CD_2Cl_2$): δ 10.52 (s, 1H), 7.92 (d, $J_{HH}$=8.8 Hz, 1H), 6.81 (d, $J_{HH}$=2.7 Hz, 1H), 6.73 (dd, $J_{HH}$=8.8, 2.7 Hz, 1H), 3.12 (s, 6H), 1.32 (s, 9H); $^{13}$C NMR (100 MHz, $CD_2Cl_2$): δ 192.0 (CH), 153.3 (C), 138.4 (C), 129.9 (CH), 127.7 (C), 121.3 (CH), 112.1 (CH), 47.1 (C), 40.0 ($CH_3$), 31.1 ($CH_3$).

Tetradentate Schiff-Base Ligands General Procedure

2-Thioertherbenzaldehyde (2 equiv.) and the appropriate diamine (1 equiv.) were dissolved in EtOH (1M) and stirred at 80° C. over night. The solvent was removed by reduced pressure and the residue was re-dissolved in EtOH. At this point either the product precipitated spontaneously or the solvent was evaporated and the residue was dried under high vacuum leaving a thick oil in quantitative yields which was sufficiently pure to be used without further purification.

N,N'-Bis(2-(methylthio)benzylidene)-1,2-ethanediamine (I) CAS: 90148-99-5

N,N'-Bis(2-(iso-propylthio)benzylidene)-1,2-ethanediamine (II)

$^1$H NMR (400 MHz, $CD_2Cl_2$): δ 8.91 (s, 2H), 8.0-7.94 (m, 2H), 7.47-7.42 (m, 2H), 7.36-7.24 (m, 4H), 3.98 (s, 4H), 3.15 (hept, $J_{HH}$=6.68 Hz, 2H), 1.15 (d, $J_{HH}$=6.68 Hz, 12H); $^{13}$C NMR (100 MHz, $CD_2Cl_2$): δ 161.4 (CH), 138.1 (C), 136.6 (C), 134.6 (CH), 130.7 (CH), 127.9 (CH), 127.9 (CH), 62.1 ($CH_2$), 40.0 (CH), 23.2 ($CH_3$).

N,N'-Bis(2-(tert-butylthio)benzylidene)-1,2-ethanediamine (IV) CAS: 123746-54-3

(R,R)—N,N'-Bis(2-(methylthio)benzylidene)-1,2-diaminocyclohexane (V)

$^1$H NMR (400 MHz, $CD_2Cl_2$): δ 8.64 (s, 2H), 7.79-7.68 (m, 2H), 7.31-7.18 (m, 4H), 7.15-7.05 (m, 2H), 3.48-3.38 (m, 2H), 2.29 (s, 6H), 1.95-1.68 (m, 6H), 1.6-1.41 (m, 2H), $^{13}$C NMR (100 MHz, $CD_2Cl_2$): δ 158.7 (CH), 139.5 (C), 135.2 (C), 130.6 (CH), 128.5 (CH), 127.8 (CH), 125.6 (CH), 74.6 (CH), 33.4 ($CH_2$), 24.9 ($CH_2$), 17.1 ($CH_3$);

(R,R)—N,N'-Bis(2-(iso-propylthio)benzylidene)-1,2-diaminocyclohexane (VI)

$^1$H NMR (400 MHz, $CD_2Cl_2$): δ8.81 (s, 2H), 7.92-7.85 (m, 2H), 7.41-7.35 (m, 2H), 7.29-7.18 (m, 4H), 3.5-3.4 (m, 2H), 3.03 (d, $J_{HH}$=6.68 Hz, 2H), 1.97-1.67 (m, 6H), 1.58-1.45 (m, 2H), 1.1 (d, $J_{HH}$=6.68 Hz, 6H), 1.02 (d, $J_{HH}$=6.68 Hz, 6H); $^{13}$C NMR (100 MHz, $CD_2Cl_2$): δ 159.4 (CH), 138.4 (C), 136.3 (C), 134.8 (CH), 130.4 (CH), 127.9 (CH), 127.9 (CH), 74.5 (CH), 40.1 (CH), 33.4 ($CH_2$), 24.9 ($CH_2$), 23.1 ($CH_3$), 23.1 ($CH_3$).

(R,R)—N,N'-Bis(2-(cyclohexylthio)benzylidene)-1,2-diaminocyclohexane (VII)

$^1$H NMR (500 MHz, $CDCl_3$): δ8.88 (s, 2H), 7.89-7.83 (m, 2H), 7.42-7.36 (m, 2H), 7.28-7.21 (m, 2H), 7.21-7.15 (m, 2H), 3.56-3.47 (m, 2H), 2.96-2.86 (m, 2H), 1.92-1.74 (m, 10H), 1.74-1.59 (m, 4H), 1.59-1.45 (m, 4H), 1.35-1.12 (m, 10H); $^{13}$C NMR (125 MHz, $CDCl_3$): δ159.9 (CH), 138.2 (C), 135.3 (C), 134.1 (CH), 130.0 (CH), 127.8 (CH), 127.5 (CH), 73.9 (CH), 48.0 (CH), 33.2 ($CH_2$), 33.1 ($CH_2$), 33.0 ($CH_2$), 25.9 ($CH_2$), 25.7 ($CH_2$), 24.5 ($CH_2$).

(R,R)—N,N'-Bis(2-(tert-butylthio)benzylidene)-1,2-diaminocyclohexane (VIII)

$^1$H NMR (400 MHz, $CD_2Cl_2$): δ8.98 (s, 2H), 8.0-7.91 (m, 2H), 7.49-7.41 (m, 2H), 7.33-7.23 (m, 4H), 3.53-3.42 (m, 2H), 1.93-1.65 (m, 6H), 1.58-1.45 (m, 2H), 1.16 (s, 18H); $^{13}$C NMR (100 MHz, $CD_2Cl_2$): δ 160.5 (CH), 141.2 (C), 139.6 (CH), 133.7 (C), 130.0 (CH), 129.4 (CH), 127.9 (CH), 74.5 (CH), 47.5 (C), 33.4 ($CH_2$), 31.2 ($CH_3$), 24.9 ($CH_2$).

(R,R)—N,N'-Bis(2-(adamant-1-ylthio)benzylidene)-1,2-diaminocyclohexane (IX)

$^1$H NMR (400 MHz, $CDCl_3$): δ9.04 (s, 2H), 7.98-7.88 (m, 2H), 7.48-7.37 (m, 2H), 7.33-7.18 (m, 4H), 3.61-3.47 (m, 2H), 2.04-1.69 (m, 24H), 1.69-1.46 (m, 14H); $^{13}$C NMR (100 MHz, $CDCl_3$): δ 161.1 (CH), 141.2 (C), 139.4 (CH), 131.1 (C), 129.4 (CH), 129.1 (CH), 127.6 (CH), 73.9 (CH), 49.4 (C), 43.7 ($CH_2$), 36.1 ($CH_2$), 32.9 ($CH_2$), 30.0 (CH), 24.6 ($CH_2$).

(R,R)—N,N'-Bis(2-(phenylthio)benzylidene)-1,2-diaminocyclohexane (X)

$^1$H NMR (400 MHz, $CDCl_3$): δ8.74 (s, 2H), 7.9-7.81 (m, 2H), 7.28-7.07 (m, 16H), 3.46-3.34 (m, 2H), 1.9-1.62 (m, 6H), 1.49-1.35 (m, 2H); $^{13}$C NMR (100 MHz, $CDCl_3$): δ 159.3 (CH), 137.1 (C), 136.4 (C), 135.2 (C), 133.2 (CH), 130.5 (CH), 130.0 (CH), 129.1 (CH), 128.4 (CH), 127.9 (CH), 126.6 (CH), 73.8 (CH), 32.7 ($CH_2$), 24.4 ($CH_2$).

(R,R)—N,N'-Bis(2-(2,6-dimethylphenylthio)benzylidene)-1,2-diaminocyclohexane (XI)

$^1$H NMR (400 MHz, $CD_2Cl_2$): δ 8.78 (s, 2H), 7.80-7.75 (m, 2H), 7.24-7.18 (m, 2H), 7.16-7.11 (m, 4H), 7.04-6.99 (m, 4H), 6.46-6.40 (m, 2H), 3.56-3.45 (m, 2H), 2.23 (s, 12H), 1.96-1.75 (m, 6H), 1.63-1.47 (m, 2H); $^{13}$C NMR (100 MHz, $CD_2Cl_2$): δ 158.3 (CH), 144.2 (C), 139.2 (C), 133.9 (C), 131.4 (C), 130.6 (CH), 129.6 (CH), 128.8 (CH), 128.6 (CH), 126.1 (CH), 125.0 (CH), 74.6 (CH), 33.5 ($CH_2$), 24.9 ($CH_2$), 21.8 ($CH_3$).

(R,R)—N,N'-Bis(2-(naphth-1-ylthio)benzylidene)-1,2-diaminocyclohexane (XII)

$^1$H NMR (400 MHz, $CD_2Cl_2$): δ 8.78 (s, 2H), 8.15-8.09 (m, 2H), 7.89-7.77 (m, 6H), 7.49-7.43 (m, 2H), 7.37-7.24 (m, 6H), 7.16-7.1 (m, 2H), 7.10-7.03 (m, 2H), 6.85-6.79 (m, 2H), 3.47-3.37 (m, 2H), 1.88-1.65 (m, 6H), 1.52-1.37 (m, 2H); $^{13}$C NMR (100 MHz, $CD_2Cl_2$): δ 159.0 (CH), 137.4 (C), 135.9 (C), 134.6 (C), 133.5 (C), 132.3 (C), 132.2 (CH), 130.9 (CH), 130.6 (CH), 129.1 (CH), 128.9 (CH), 127.2 (CH), 126.8 (CH), 126.8 (CH), 126.2 (CH), 125.6 (CH), 74.6 (CH), 33.3 ($CH_2$), 24.8 ($CH_2$).

(R,R)—N,N'-Bis(2-(4-tert-butylphenylthio)benzylidene)-1,2-diaminocyclohexane (XIII)

$^{1}$H NMR (400 MHz, $CD_2Cl_2$): δ 8.69 (s, 2H), 7.86-7.79 (m, 2H), 7.29-7.14 (m, 10H), 7.14-7.08 (m, 4H), 3.40-3.28 (m, 2H), 1.85-1.73 (m, 2H), 1.73-1.57 (m, 4H), 1.51-1.35 (m, 2H), 1.27 (s, 18H); $^{13}$C NMR (100 MHz, $CD_2Cl_2$): δ 159.1 (CH), 150.8 (C), 137.0 (C), 136.9 (C), 132.8 (C), 132.7 (CH), 131.1 (CH), 130.7 (CH), 128.6 (CH), 127.7 (CH), 126.7 (CH), 74.3 (CH), 34.8 (C), 33.2 ($CH_2$), 31.4 ($CH_3$), 24.8 ($CH_2$).

(R,R)—N,N'-Bis(2-(4-fluorophenylthio)benzylidene)-1,2-diaminocyclohexane (XIV)

$^{1}$H NMR (500 MHz, $CD_2Cl_2$): δ 8.67 (s, 2H), 7.83-7.77 (m, 2H), 7.26-7.12 (m, 8H), 7.12-7.07 (m, 2H), 6.98-6.89 (m, 4H), 3.44-3.34 (m, 2H), 1.89-1.78 (m, 2H), 1.78-1.66 (m, 4H), 1.52-1.42 (m, 2H); $^{13}$C NMR (125 MHz, $CD_2Cl_2$): δ 162.6 (d, $J_{CF}$=246.7 Hz, CF), 159.0 (CH), 136.8 (d, $J_{CF}$=47.4 Hz, C), 133.8 (d, $J_{CF}$=8.1 Hz, CH), 131.5 (d, $J_{CF}$=172.3 Hz, CH), 131.3 (d, $J_{CF}$=3.6 Hz, C), 128.3 (d, $J_{CF}$=161.2 Hz, CH), 116.7 (d, $J_{CF}$=21.8 Hz, CH), 74.5 (CH), 33.3 ($CH_2$), 24.8 ($CH_2$); $^{19}$F NMR (376.5 MHz, $CD_2Cl_2$): δ-111.5 (s, 2F).

(R,R)—N,N'-Bis(2-(tert-butylthio)-4-(trifluoromethyl)benzylidene)-1,2-diaminocyclohexane (XV)

$^{1}$H NMR (400 MHz, $CD_2Cl_2$): δ 8.98 (s, 2H), 8.15-8.06 (m, 2H), 7.76-7.69 (m, 2H), 7.59-7.51 (m, 2H), 3.59-3.48 (m, 2H), 1.98-1.65 (m, 8H), 1.6-1.45 (m, 2H), 1.17 (s, 18H); $^{13}$C NMR (100 MHz, $CD_2Cl_2$): δ 159.5 (CH), 144.3 (C), 136.2 (q, $J_{CF}$=3.7 Hz, CH), 134.8 (C), 131.6 (q, $J_{CF}$=32.4 Hz, C), 128.5 (CH), 125.9 (q, $J_{CF}$=3.7 Hz, CH), 124.2 (q, $J_{CF}$=272.3 Hz, $CF_3$), 74.5 (CH), 48.3 (C), 33.2 ($CH_2$), 31.1 ($CH_3$), 24.8 ($CH_2$).

(R,R)—N,N'-Bis(2-(tert-butylthio)-4-bromobenzylidene)-1,2-diaminocyclohexane (XVI)

$^{1}$H NMR (400 MHz, $CD_2Cl_2$): δ 8.87 (s, 2H), 7.88-7.81 (m, 2H), 7.66-7.6 (m, 2H), 7.47-7.4 (m, 2H), 3.52-3.39 (m, 2H), 1.91-1.64 (m, 6H), 1.56-1.44 (m, 2H), 1.18 (s, 18H); $^{13}$C NMR (100 MHz, $CD_2Cl_2$): δ 159.6 (CH), 141.5 (CH), 140.1 (C), 135.7 (C), 132.6 (CH), 129.4 (CH), 123.8 (C), 74.5 (CH), 48.2 (C), 33.3 ($CH_2$), 31.1 ($CH_3$), 24.8 ($CH_2$).

(R,R)—N,N'-Bis((3-(tert-butylthio)-[1,1'-biphenyl]-4-yl)methylene)-1,2-diaminocyclohexane (XVII)

$^{1}$H NMR (400 MHz, $CD_2Cl_2$): δ 9.02 (s, 2H), 8.10-8.04 (m, 2H), 7.73-7.69 (m, 2H), 7.6-7.52 (m, 6H), 7.46-7.38 (m, 4H), 7.38-7.30 (m, 2H), 3.57-3.47 (m, 2H), 1.93-1.71 (m, 6H), 1.61-1.48 (m, 2H), 1.22 (s, 18H); $^{13}$C NMR (100 MHz, $CD_2Cl_2$): δ 160.2 (CH), 142.7 (C), 140.2 (C), 140.0 (C), 138.0 (CH), 134.2 (C), 129.2 (CH), 128.4 (CH), 128.2 (CH), 128.0 (CH), 127.4 (CH), 74.7 (CH), 47.7 (C), 33.4 ($CH_2$), 31.2 ($CH_3$), 24.9 ($CH_2$).

(R,R)—N,N'-Bis(2-(tert-butylthio)-4-tert-butylbenzylidene)-1,2-diaminocyclohexane (XVIII)

$^{1}$H NMR (400 MHz, $CD_2Cl_2$): δ 8.97 (s, 2H), 7.97-7.9 (m, 2H), 7.54-7.49 (m, 2H), 7.41-7.34 (m, 2H), 3.56-3.44 (m, 2H), 1.95-1.71 (m, 6H), 1.61-1.50 (m, 2H), 1.32 (s, 18H), 1.20 (s, 18H); $^{13}$C NMR (100 MHz, $CD_2Cl_2$): δ 160.3 (CH), 153.4 (C), 138.4 (C), 136.7 (CH), 133.2 (C), 127.5 (CH), 126.6 (CH), 74.5 (CH), 47.3 (C), 34.8 (C), 33.5 ($CH_2$), 31.2 ($CH_3$), 25.0 ($CH_2$).

(R,R)—N,N'-Bis(2-(tert-butylthio)-4,5-dimethoxybenzylidene)-1,2-diaminocyclohexane (XIX)

$^{1}$H NMR (400 MHz, $CDCl_3$): δ8.88 (s, 2H), 7.51 (s, 2H), 6.91 (s, 2H), 3.87 (s, 6H), 3.86 (s, 6H), 3.51-3.42 (m, 2H), 1.92-1.71 (m, 6H), 1.58-1.46 (m, 2H), 1.15 (s, 18H); $^{13}$C NMR (100 MHz, $CDCl_3$): δ 160.2 (CH), 149.9 (C), 149.8 (C), 134.4 (C), 125.4 (C), 120.9 (CH), 109.4 (CH), 73.9 (CH), 56.0 ($CH_3$), 56.0 ($CH_3$), 47.2 (C), 33.0 ($CH_2$), 30.9 ($CH_3$), 24.6 ($CH_2$).

(R,R)—N,N'-Bis(2-(4-(tert-butylphenyl)thio)-4,5-dimethoxybenzylidene)-1,2-diaminocyclohexane (XXI)

$^{1}$H NMR (400 MHz, $CD_2Cl_2$): δ 8.66 (s, 2H), 7.48 (s, 2H), 7.21-7.14 (m, 4H), 6.98-6.92 (m, 4H), 6.84 (s, 2H), 3.80 (s, 6H), 3.73 (s, 6H), 3.34-3.25 (m, 2H), 1.85-1.72 (m, 2H), 1.72-1.56 (m, 4H), 1.48-1.33 (m, 2H), 1.25 (s, 18H), $^{13}$C NMR (100 MHz, $CD_2Cl_2$): δ 159.1 (CH), 151.6 (C), 150.2 (C), 149.7 (C), 134.9 (C), 132.0 (C), 128.4 (CH), 126.5 (C), 126.5 (CH), 117.5 (CH), 110.0 (CH), 73.9 (CH), 56.2 ($CH_3$), 56.2 ($CH_3$), 34.7 (C), 33.3 ($CH_2$), 31.3 ($CH_3$), 24.9 ($CH_2$).

(1R,2R)—N,N'-bis(2,6-bis(tert-butylthio)benzylidene)-1,2-diaminocyclohexane (XXII)

$^{1}$H NMR (400 MHz, $CD_2Cl_2$): δ 8.71 (s, 2H), 7.56 (d, $J_{HH}$=7.72 Hz, 4H), 7.25 (t, $J_{HH}$=7.72 Hz, 2H), 3.65-3.57 (m, 2H), 1.98-1.45 (m, 8H), 1.19 (s, 36H); $^{13}$C NMR (100 MHz, $CD_2Cl_2$): δ 160.5 (CH), 148.0 (C), 138.5 (CH), 134.2 (C), 127.7 (CH), 74.4 (CH), 47.8 (C), 32.2 ($CH_2$), 31.3 ($CH_3$), 23.9 ($CH_2$).

(1R,2R)—N,N'-bis((1-tert-butylthionaphthalen-2-yl)methylene)-1,2-diaminocyclohexane (XXIII)

$^{1}$H NMR (400 MHz, Toluene-$d_6$, 60° C.): δ 9.60 (s, 2H), 8.93 (d, $J_{HH}$=8.7 Hz, 2H), 8.48 (d, $J_{HH}$=8.8 Hz, 2H), 7.53 (d, $J_{HH}$=8.7 Hz, 2H), 7.45 (d, $J_{HH}$=8.0 Hz, 2H), 7.32-7.23 (m, 2H), 7.23-7.13 (m, 2H), 3.86-3.66 (m, 2H), 2.05-1.70 (m, 6H), 1.56-1.40 (m, 2H), 1.07 (s, 18H); $^{13}$C NMR (100 MHz, Toluene-$d_6$): δ161.7 (CH), 141.0 (C), 138.0 (C), 135.5 (C), 133.4 (C), 129.5 (CH), 128.5 (CH), 128.4 (CH), 127.0 (CH), 126.4 (CH), 125.6 (CH), 75.1 (CH), 49.4 (C), 33.6 ($CH_2$), 31.8 ($CH_3$), 25.0 ($CH_2$).

N,N'-Bis(2-(tert-butylthio)benzylidene)propane-1,3-diamine (XXXII)

$^{1}$H NMR (400 MHz, $CD_2Cl_2$): δ 9.11 (s, 2H), 8.11 (dd, $J_{HH}$=7.6, 1.7 Hz, 2H), 7.56 (dd, $J_{HH}$=7.4, 1.4 Hz, 2H), 7.46-7.34 (m, 4H), 3.74 (td, $J_{HH}$=3.5, 1.0 Hz, 4H), 2.06 (pent, $J_{HH}$=6.9 Hz, 2H), 1.24 (s, 18H); $^{13}$C NMR (100 MHz, $CD_2Cl_2$): δ 161.6 (CH), 141.2 (C), 139.9 (CH), 133.8 (C), 130.2 (CH), 129.6 (CH), 127.7 (CH), 59.6 ($CH_2$), 47.6 (C), 32.7 ($CH_2$), 31.2 ($CH_3$).

N,N'-Bis(2-(tert-butylthio)benzylidene)-2,2-dimethylpropane-1,3-diamine (XXXIII)

$^{1}$H NMR (400 MHz, $CD_2Cl_2$): δ9.09 (s, 2H), 8.18 (dd, $J_{HH}$=7.7, 1.8 Hz, 2H), 7.56 (dd, $J_{HH}$=7.6, 1.4 Hz, 2H), 7.47-

7.34 (m, 4H), 3.56 (d, $J_{HH}$=1.3 Hz, 4H), 1.24 (s, 18H), 1.02 (s, 6H); $^{13}$C NMR (100 MHz, $CD_2Cl_2$): δ 161.5 (CH), 141.3 (C), 139.9 (CH), 133.8 (C), 130.2 (CH), 129.6 (CH), 127.9 (CH), 70.7 ($CH_2$), 47.5 (C), 37.6 (C), 31.2 ($CH_3$), 24.9 ($CH_3$).

(R,R)—N,N'-Bis(2-(tert-butylthio)-5-nitrobenzylidene)-1,2-diaminocyclohexane (XXXIV)

$^1$H NMR (400 MHz, $CD_2Cl_2$): δ 8.94 (s, 2H), 8.78 (d, $J_{HH}$=2.6 Hz, 2H), 8.06 (dd, $J_{HH}$=8.5, 2.8 Hz, 2H), 7.63 (d, $J_{HH}$=8.5 Hz, 2H), 3.64-3.52 (m, 2H), 2.00-1.73 (m, 6H), 1.61-1.47 (m, 2H), 1.16 (s, 18H); $^{13}$C NMR (100 MHz, $CD_2Cl_2$): δ 158.7 (CH), 148.6 (C), 142.2 (C), 141.9 (C), 140.0 (CH), 123.7 (CH), 122.5 (CH), 74.3 (CH), 49.3 (C), 33.1 ($CH_2$), 31.1 ($CH_3$), 24.7 ($CH_2$).

(R,R)—N,N'-Bis(2-(tert-butylthio)-5-(dimethylamino)benzylidene)-1,2-diaminocyclohexane (XXXV)

$^1$H NMR (400 MHz, $CD_2Cl_2$): δ 8.89 (s, 2H), 6.75 (d, $J_{HH}$=2.8 Hz, 2H), 6.62 (dd, $J_{HH}$=8.8, 2.7 Hz, 2H), 2.94 (s, 12H), 1.22 (s, 18H); $^{13}$C NMR (100 MHz, $CD_2Cl_2$): δ 160.7 (CH), 151.0 (C), 134.1 (C), 128.7 (C), 121.7 (CH), 113.1 (CH), 74.0 (CH), 47.0 (C), 40.2 ($CH_3$), 33.3 ($CH_2$), 31.2 ($CH_3$), 24.7 ($CH_2$).

(R)—N,N'-Bis(2-(tert-butylthio)benzylidene)propane-1,2-diamine (XXXVI)

$^1$H NMR (400 MHz, $CD_2Cl_2$): δ 9.07 (s, 1H), 9.04 (s, 1H), 8.09-8.02 (m, 2H), 7.54-7.50 (m, 2H), 7.41-7.31 (m, 4H), 3.89-3.73 (m, 3H), 1.32 (d, $J_{HH}$=6.0 Hz, 3H), 1.21 (s, 9H), 1.20 (s, 9H); $^{13}$C NMR (100 MHz, $CD_2Cl_2$): δ 162.5 (CH), 160.6 (CH), 141.1 (C), 141.0 (C), 139.8 (CH), 133.9 (C), 133.9 (C), 130.3 (CH), 130.2 (CH), 129.6 (CH), 129.5 (CH), 127.9 (CH), 127.8 (CH), 68.4 ($CH_2$), 67.0 (CH), 47.6 (C), 47.6 (C), 31.2 ($CH_3$), 20.8 ($CH_3$).

General Procedure for the Synthesis of the Diamine Tetradentate Ligands XXIV-XXXI The appropriate Schiff-base ligand was added to a suspension of $NaBH_4$ (2.2 equiv.) in EtOH (1M) at room temperature. The mixture was refluxed while stirring for 4 h, then cooled to room temperature. NaOH solution (5 w/w-% in $H_2O$) was added and the stirring was continued for 30 min The mixture was diluted with MTBE and extracted. The organic layer was washed with $K_2CO_3$ sat. aqueous solution and dried with $MgSO_4$. The solvent was evaporated and the residue purified by column chromatography (Silicagel, Hept/EtOAc 5:1 with 2% $Et_3N$).

(1R,2R)—N,N'-Bis(2-(cyclohexylthio)benzyl)-1,2-diaminocyclohexane (XXIV)

$^1$H NMR (400 MHz, $CDCl_3$): δ 7.46-7.34 (m, 4H), 7.21-7.12 (m, 4H), 4.01 (d, $J_{HH}$13.41 Hz, 2H), 3.81 (d, $J_{HH}$=13.41 Hz, 2H), 3.15-3.00 (m, 2H), 2.32-2.13 (m, 4H), 2.09-1.84 (m, 6H), 1.82-1.64 (m, 6H), 1.64-1.52 (m, 2H), 1.45-1.15 (m, 12H), 1.15-0.97 (m, 2H); $^{13}$C NMR (100 MHz, $CDCl_3$): δ 142.1 (C), 134.4 (C), 131.7 (CH), 129.2 (CH), 127.0 (CH), 126.5 (CH), 61.1 (CH), 49.1 ($CH_2$), 46.6 (CH), 33.4 ($CH_2$), 31.7 ($CH_2$), 26.1 ($CH_2$), 25.8 ($CH_2$), 25.1 ($CH_2$).

(1R,2R)—N,N'-Bis(2-(tert-butylthio)benzyl)-1,2-diaminocyclohexane (XXV)

$^1$H NMR (400 MHz, $CDCl_3$): δ 7.56-7.48 (m, 4H), 7.35-7.27 (m, 2H), 7.18 (d, $J_{HH}$=13.4 Hz, 2H), 4.14 (d, JHH=13.4 Hz, 2H), 3.97-3.85 (m, 2H), 2.28-2.12 (m, 4H), 1.98 (s, 2H), 1.81-1.62 (m, 2H), 1.35-1.15 (m, 20H), 1.13-0.95 (m, 2H); $^{13}$C NMR (100 MHz, $CDCl_3$): δ 146.2 (C), 138.7 (CH), 131.8 (C), 129.4 (CH), 129.0 (CH), 126.5 (CH), 61.0 (CH), 49.4 ($CH_2$), 47.0 (C), 31.8 ($CH_2$), 31.2 ($CH_3$), 25.1 ($CH_2$).

(1R,2R)—N,N'-Bis(2-(phenylthio)benzyl)-1,2-diaminocyclohexane (XXVI)

$^1$H NMR (400 MHz, $CDCl_3$): δ7.49-7.44 (m, 2H), 7.28-7.12 (m, 16H), 3.99 (d, $J_{HH}$=13.44 Hz, 2H), 3.8 (d, $J_{HH}$=13.44 Hz, 2H), 2.30-2.17 (m, 2H), 2.17-2.06 (m, 2H), 2.06-1.87 (m, 2H), 1.73-1.60 (m, 2H), 1.24-1.13 (m, 2H), 1.07-0.92 (m, 2H); $^{13}$C NMR (100 MHz, $CDCl_3$): δ 142.2 (C), 136.4 (C), 134.1 (C), 132.9 (CH), 130.2 (CH), 129.6 (CH), 129.1 (CH), 127.7 (CH), 127.6 (CH), 126.5 (CH), 61.1 (CH), 49.1 ($CH_2$), 31.6 ($CH_2$), 25.0 ($CH_2$).

(1R,2R)—N,N'-Bis(2-(naphth-1-yl)benzyl)-1,2-diaminocyclohexane (XXVII)

$^1$H NMR (400 MHz, $CD_2Cl_2$): δ 8.21 (d, $J_{HH}$=8.32 Hz, 2H), 7.86 (d, $J_{HH}$=7.96 Hz, 2H), 7.79 (d, $J_{HH}$=7.92 Hz, 2H), 7.58-7.39 (m, 6H), 7.39-7.27 (m, 4H), 7.12 (t, $J_{HH}$=7.32 Hz, 2H), 7.01 (t, $J_{HH}$=7.28 Hz, 2H), 6.87 (d, $J_{HH}$=7.64 Hz, 2H), 4.14 (d, $J_{HH}$=13.4 Hz, 2H), 3.94 (d, $J_{HH}$=13.4 Hz, 2H), 2.45-2.33 (m, 2H), 2.23-2.09 (m, 2H), 1.78-1.60 (m, 2H), 1.43-1.01 (m, 4H), 0.94-0.76 (m, 2H). $^{13}$C NMR (100 MHz, $CD_2Cl_2$): δ 139.8 (C), 135.8 (C), 134.6 (C), 133.4 (C), 132.1 (C), 131.8 (CH), 131.0 (CH), 130.2 (CH), 129.0 (CH), 129.0 (CH), 128.3 (CH), 127.2 (CH), 126.8 (CH), 126.2 (CH), 125.6 (CH), 61.2 (CH), 49.1 ($CH_2$), 31.3 ($CH_2$), 25.2 ($CH_2$).

(1R,2R)—N,N'-Bis(2-(tert-butylthio)benzyl)-1,2-diphenylethane-1,2-diamine (XXXI)

$^1$H NMR (400 MHz, $CDCl_3$): δ 7.50-7.43 (m, 2H), 7.40-7.33 (m, 2H), 7.31-7.23 (m, 2H), 7.21-7.04 (m, 12H), 3.86 (d, $J_{HH}$=13.36 Hz, 2H), 3.70 (d, $J_{HH}$=13.36 Hz, 2H), 3.69 (s, 2H), 1.32 (s, 2H), 1.14 (s, 18H); $^{13}$C NMR (100 MHz, $CDCl_3$): δ 145.7 (C), 141.3 (C), 138.7 (CH), 131.9 (C), 129.8 (CH), 128.8 (CH), 128.1 (CH), 127.8 (CH), 126.7 (CH), 126.6 (CH), 68.8 (CH), 50.4 ($CH_2$), 47.0 (C), 31.0 ($CH_3$).

General Procedure for the Synthesis of the Ruthenium Dichloro Complexes.

An equimolar mixture of $RuCl_2(PPh_3)_3$ and the appropriate tetradentate ligand was dissolved in toluene (0.5-1 M) under nitrogen and stirred at 80° C. over night. After cooling at room temperature, the mixture was concentrated and the complex was precipitated with the addition of $Et_2O$ or hexane. Alternatively, the crude ruthenium complex was purified by filtration through aluminum oxide rinsing first with toluene, then with $CH_2Cl_2$ to elute the complex.

(R,R)—$RuCl_2$(I)

$^1$H NMR (400 MHz, $CD_2Cl_2$): δ 8.90 (s, 2H), 7.92-7.80 (m, 2H), 7.67-7.44 (m, 6H), 4.24 (s, 4H), 2.68 (s, 6H); $^{13}$C NMR (100 MHz, $CD_2Cl_2$): δ 161.9 (CH), 136.8 (CH), 135.3 (C), 133.8 (CH), 132.6 (CH), 129.6 (CH), 128.8 (C), 64.6 ($CH_2$), 28.2 ($CH_3$).

(R,R)—$RuCl_2$(II)

$^1$H NMR (400 MHz, $CD_2Cl_2$): d 8.90 (s, 2H), 7.81-7.74 (m, 2H), 7.63-7.52 (m, 6H), 4.19 (s, 4H), 3.52 (hept, $J_{HH}$=6.7 Hz, 2H), 1.19 (d, $J_{HH}$=6.7 Hz, 12H); $^{13}$C NMR (100 MHz, $CD_2Cl_2$): δ 162.2 (CH), 138.1 (C), 136.4 (CH), 136.4 (CH), 131.6 (CH), 130.1 (CH), 123.8 (C), 64.9 ($CH_2$), 46.6 (CH), 22.0 ($CH_3$).

(R,R)—$RuCl_2$(III)

$^1$H NMR (400 MHz, $CD_2Cl_2$): δ 8.76 (s, 2H), 7.80-7.73 (m, 2H), 7.65-7.52 (m, 6H), 3.93-3.81 (m, 2H), 3.23-3.10 (m, 2H), 2.83-2.69 (m, 2H), 2.26-2.12 (m, 2H), 2.12-2.01 (m, 2H), 2.01-1.88 (m, 2H), 1.78-1.59 (m, 6H), 1.56-1.38 (m, 6H), 1.38-1.21 (m, 2H), 1.21-1.07 (m, 2H), 1.04-0.89 (m, 2H), 0.78-0.64 (m, 2H); $^{13}$C NMR (100 MHz, $CD_2Cl_2$): δ 159.3 (CH), 139.0 (C), 136.7 (CH), 136.2 (CH), 131.3 (CH), 129.9 (CH), 122.8 (C), 72.1 (CH), 53.6 (CH), 33.3 ($CH_2$), 31.4 ($CH_2$), 31.3 ($CH_2$), 27.2 ($CH_2$), 26.5 ($CH_2$), 25.8 ($CH_2$), 24.9 ($CH_2$).

(R,R)—$RuCl_2$(IV) CAS: 208832-52-4

(R,R)—$RuCl_2$(V)

$^1$H NMR (400 MHz, $CD_2Cl_2$): d 8.80 (s, 2H), 7.89-7.80 (m, 2H), 7.66-7.56 (m, 4H), 7.56-7.48 (m, 2H), 4.00-3.86 (m, 2H), 2.87-2.75 (m, 2H), 2.72-2.57 (m, 6H), 2.15-2.00 (m, 2H), 2.00-1.84 (m, 2H), 1.57-1.40 (m, 2H); $^{13}$C NMR (100 MHz, $CD_2Cl_2$): δ 159.0 (CH), 137.4 (CH), 136.0 (C), 133.5 (CH), 132.5 (CH), 129.6 (CH), 128.4 (C), 72.4 (CH), 31.1 ($CH_2$), 27.8 ($CH_3$), 25.0 ($CH_2$).

(R,R)—$RuCl_2$(VI)

$^1$H NMR (400 MHz, $CD_2Cl_2$): δ 8.74 (s, 2H), 7.80-7.74 (m, 2H), 7.69-7.44 (m, 8H), 3.93-3.81 (m, 2H), 3.47 (hept, $J_{HH}$=6.7 Hz, 2H), 2.84-2.71 (m, 2H), 2.14-2.01 (m, 2H), 2.01-1.85 (m, 2H), 1.43 (d, $J_{HH}$=6.7 Hz, 6H), 0.91 (d, $J_{HH}$=6.7 Hz, 6H); $^{13}$C NMR (100 MHz, $CD_2Cl_2$): δ 159.5 (CH), 138.9 (C), 137.0 (CH), 136.1 (CH), 131.5 (CH), 130.0 (CH), 123.0 (C), 72.1 (CH), 46.2 (CH), 31.3 ($CH_2$), 24.9 ($CH_2$), 22.9 ($CH_3$), 21.1 ($CH_3$).

(R,R)—$RuCl_2$(VII)

$^1$H NMR (400 MHz, $CD_2Cl_2$): δ 8.76 (s, 2H), 7.80-7.73 (m, 2H), 7.65-7.52 (m, 6H), 3.93-3.81 (m, 2H), 3.22-3.10 (m, 2H), 2.82-2.69 (m, 2H), 2.23-2.13 (m, 2H), 2.13-2.01 (m, 2H), 2.01-1.88 (m, 2H), 1.78-1.59 (m, 6H), 1.56-1.38 (m, 6H), 1.36-1.21 (m, 2H), 1.21-1.07 (m, 2H), 1.05-0.90 (m, 2H), 0.78-0.64 (m, 2H); $^{13}$C NMR (100 MHz, $CD_2Cl_2$): δ 159.3 (CH), 139.0 (C), 136.7 (CH), 136.2 (CH), 131.3 (CH), 129.9 (CH), 122.8 (C), 72.1 (CH), 53.6 (CH), 33.3 ($CH_2$), 31.4 ($CH_2$), 31.3 ($CH_2$), 27.2 ($CH_2$), 26.5 ($CH_2$), 25.8 ($CH_2$), 24.9 ($CH_2$).

(R,R)—$RuCl_2$(VIII) CAS: 208832-56-8

(R,R)—$RuCl_2$(X)

$^1$H NMR (400 MHz, $CD_2Cl_2$): δ 8.79 (s, 2H), 7.66-7.57 (m, 2H), 7.47-7.40 (m, 2H), 7.40-7.27 (m, 8H), 7.27-7.20 (m, 2H), 7.20-7.13 (m, 4H), 3.97-3.86 (m, 2H), 2.89-2.75 (m, 2H), 2.18-2.04 (m, 2H), 2.04-1.87 (m, 2H), 1.57-1.42 (m, 2H); $^{13}$C NMR (100 MHz, $CD_2Cl_2$): δ 160.3 (CH), 137.6 (C), 137.2 (CH), 134.7 (C), 133.8 (CH), 133.0 (CH), 132.3 (CH), 129.7 (C), 129.5 (CH), 129.2 (CH), 128.9 (CH), 71.7 (CH), 31.3 ($CH_2$), 25.0 ($CH_2$);

(R,R)—$RuCl_2$(XIV)

$^1$H NMR (400 MHz, $CD_2Cl_2$): δ 8.81 (s, 2H), 7.64-7.59 (m, 2H), 7.54-7.45 (m, 4H), 7.45-7.38 (m, 2H), 7.38-7.31 (m, 2H), 7.17-7.07 (m, 2H), 6.94-6.83 (m, 4H), 3.97-3.85 (m, 2H), 2.90-2.76 (m, 2H), 2.18-2.06 (m, 2H), 2.04-1.91 (m, 2H), 1.59-1.44 (m, 2H); $^{13}$C NMR (100 MHz, $CD_2Cl_2$): δ 165.1 (C), 162.6 (C), 160.4 (CH), 137.4 (CH), 136.4 (CH), 136.3 (CH), 134.0 (C), 132.8 (C), 132.8 (C), 132.4 (CH), 130.3 (C), 128.8 (CH), 116.4 (CH), 116.2 (CH), 71.5 (CH), 31.3 ($CH_2$), 24.9 ($CH_2$); $^{19}$F NMR (376.5 MHz, $CD_2Cl_2$): δ-111.3 (s, 2F).

(R,R)—$RuCl_2$(XV)

$^1$H NMR (400 MHz, $CD_2Cl_2$): δ 8.81 (s, 2H), 7.97 (s, 2H), 7.90-7.72 (m, 4H), 4.02-3.91 (m, 2H), 2.78-2.66 (m, 2H), 2.13-1.87 (m, 4H), 1.49-1.41 (m, 2H), 1.37 (s, 18H); $^{13}$C NMR (100 MHz, $CD_2Cl_2$): δ 160.1 (CH), 142.5 (C), 136.6 (CH), 133.9 (q, $T_{CF}$=3.7 Hz, CH), 131.8 (q, $J_{CF}$=33.2 Hz, C), 126.7 (q, $J_{CF}$=3.5 Hz, CH), 125.7 (C), 123.9 (q, $J_{CF}$=269.0 Hz, $CF_3$), 72.5 (CH), 57.4 (C), 31.7 ($CH_2$), 28.9 ($CH_3$), 24.7 ($CH_2$); $^{19}$F NMR (376.5 MHz, $CD_2Cl_2$): δ-63.27 (s, 6F).

(R,R)—$RuCl_2$(XVI)

$^1$H NMR (400 MHz, $CDCl_3$): δ8.68 (s, 2H), 7.92-7.84 (m, 2H), 7.67-7.63 (m, 2H), 7.46-7.40 (m, 2H), 4.04-3.93 (m, 2H), 2.77-2.62 (m, 2H), 2.10-1.85 (m, 4H), 1.43-1.38 (m, 2H), 1.41 (s, 18H); $^{13}$C NMR (100 MHz, $CDCl_3$): δ 159.6 (CH), 139.4 (CH), 137.5 (C), 137.1 (CH), 132.6 (CH), 125.9 (C), 124.0 (C), 71.4 (CH), 56.9 (C), 31.1 ($CH_2$), 29.0 ($CH_3$), 24.3 ($CH_2$), (R,R)—$RuCl_2$(XVII)

$^1$H NMR (400 MHz, $CD_2Cl_2$): δ 8.80 (s, 2H), 8.00 (s, 2H), 7.91-7.78 (m, 2H), 7.78-7.64 (m, 6H), 7.61-7.38 (m, 6H), 4.08-3.87 (m, 2H), 2.84-2.66 (m, 2H), 2.16-1.89 (m, 4H), 1.63-1.37 (m, 2H), 1.42 (s, 18H); $^{13}$C NMR (100 MHz, $CD_2Cl_2$): δ 160.2 (CH), 143.2 (C), 139.5 (C), 138.1 (C), 136.9 (CH), 135.7 (CH), 129.4 (CH), 128.7 (CH), 128.1 (CH), 127.5 (CH), 125.4 (C), 72.0 (CH), 56.4 (C), 31.7 ($CH_2$), 29.2 ($CH_3$), 24.9 ($CH_2$).

(R,R)—$RuCl_2$(XVIII)

$^1$H NMR (400 MHz, $CD_2Cl_2$): δ 8.71 (s, 2H), 7.77-7.69 (m, 2H), 7.62-7.51 (m, 4H), 3.98-3.84 (m, 2H), 2.80-2.63 (m, 2H), 2.12-1.97 (m, 2H), 1.97-1.83 (m, 2H), 1.83-1.64 (m, 2H), 1.39 (s, 18H), 1.36 (s, 18H); $^{13}$C NMR (100 MHz, $CD_2Cl_2$): δ 160.3 (CH), 154.4 (C), 136.4 (C), 136.3 (CH), 134.3 (CH), 126.9 (CH), 124.7 (C), 71.6 (CH), 56.0 (C), 35.3 (C), 31.7 ($CH_2$), 31.1 ($CH_3$), 29.2 ($CH_3$), 24.9 ($CH_2$).

(R,R)—$RuCl_2$(XIX)

$^1$H NMR (400 MHz, $CD_2Cl_2$): δ 8.62 (s, 2H), 7.23 (s, 2H), 7.07 (s, 2H), 3.96 (s, 6H), 3.94 (s, 6H), 3.93-3.85 (m, 2H), 2.77-2.66 (m, 2H), 2.11-1.85 (m, 4H), 1.58-1.41 (m, 2H), 1.37 (s, 18H); $^{13}$C NMR (100 MHz, $CD_2Cl_2$): δ 159.6 (CH), 150.2 (C), 150.0 (C), 132.2 (C), 119.8 (CH), 118.7 (CH), 117.7 (C), 71.5 (CH), 56.5 ($CH_3$), 56.4 ($CH_3$), 56.1 (C), 31.7 ($CH_2$), 29.3 ($CH_3$), 24.9 ($CH_2$).

(R,R)—$RuCl_2$(XXI)

$^1$H NMR (400 MHz, $CD_2Cl_2$): δ 8.72 (s, 2H), 7.41-7.09 (m, 12H), 3.90 (s, 6H), 3.58 (s, 6H), 2.89-2.77 (m, 2H), 2.17-2.03 (m, 2H), 2.03-1.87 (m, 2H), 1.87-1.68 (m, 2H), 1.57-1.43 (m, 2H), 1.30 (s, 18H); $^{13}$C NMR (100 MHz, $CD_2Cl_2$): δ 158.9

(CH), 152.5 (C), 151.8 (C), 149.4 (C), 135.0 (CH), 133.8 (C), 133.2 (CH), 132.8 (C), 128.6 (C), 126.0 (CH), 118.9 (CH), 71.3 (CH), 56.5 ($CH_3$), 56.1 ($CH_3$), 35.0 (C), 31.4 ($CH_3$), 31.3 ($CH_2$), 25.0 ($CH_2$), (R,R)—$RuCl_2$(XXII)

$^1$H NMR (400 MHz, $CD_2Cl_2$): δ 10.12 (s, 2H), 7.86-7.74 (m, 4H), 7.50 (dd, $J_{HH}$=7.83 Hz, $J_{HH}$=7.83 Hz, 2H), 4.07-3.93 (m, 2H), 2.80-2.67 (m, 2H), 2.16-1.92 (m, 4H), 1.49-1.39 (m, 2H), 1.36 (s, 18H), 1.32 (s, 18H); $^{13}$C NMR (100 MHz, $CD_2Cl_2$): δ 162.6 (CH), 142.7 (C), 142.0 (CH), 139.1 (C), 139.0 (CH), 129.3 (CH), 125.9 (C), 73.5 (CH), 56.4 (C), 49.0 (C), 32.4 ($CH_2$), 31.4 ($CH_3$), 29.1 ($CH_3$), 25.0 ($CH_2$).

(R,R)—$RuCl_2$(XXV)

$^1$H NMR (400 MHz, $CD_2Cl_2$): δ 7.72-7.64 (m, 2H), 7.50-7.34 (m, 6H), 4.79 (t, $J_{HH}$=11.5 Hz, 2H), 4.17 (d, $J_{HH}$=11.5 Hz, 2H), 3.66-3.52 (m, 2H), 2.93-2.82 (m, 2H), 2.82-2.71 (m, 2H), 1.90-1.75 (m, 2H), 1.43 (s, 18H), 1.32-1.24 (m, 2H), 1.20-1.05 (m, 2H); $^{13}$C NMR (100 MHz, $CD_2Cl_2$): δ 142.7 (C), 137.1 (CH), 131.7 (CH), 130.2 (CH), 129.5 (C), 128.7 (CH), 65.1 (CH), 54.4 (C), 53.4 ($CH_2$), 31.3 ($CH_2$), 30.1 ($CH_3$), 25.1 ($CH_2$).

(R,R)—$RuCl_2$(XXVI)

$^1$H NMR (400 MHz, $CD_2Cl_2$): δ 7.74-7.49 (m, 4H), 7.42-7.33 (m, 2H), 7.33-7.23 (m, 4H), 7.23-7.10 (m, 6H), 6.83 (s, 2H), 4.78 (t, $J_{HH}$=11.6 Hz, 2H), 4.24 (d, $J_{HH}$=11.6 Hz, 2H), 4.30-4.12 (m, 2H), 3.10-2.93 (m, 2H), 2.93-2.78 (m, 2H), 2.00-1.81 (m, 2H), 1.46-1.15 (m, 4H); $^{13}$C NMR (100 MHz, $CD_2Cl_2$): δ 136.9 (C), 135.1 (C), 133.9 (CH), 132.1 (CH), 129.8 (CH), 129.4 (CH), 129.4 (CH), 128.3 (CH), 64.9 (CH), 52.5 ($CH_2$), 31.3 ($CH_2$), 25.2 ($CH_2$).

$RuCl_2$(XXXII)

$^1$H NMR (400 MHz, $CD_2Cl_2$): δ 8.64 (s, 2H), 7.75-7.60 (m, 2H), 7.60-7.42 (m, 4H), 7.42-7.22 (m, 2H), 5.18-4.95 (m, 2H), 3.97-3.83 (m, 2H), 2.38-2.18 (m, 2H), 1.32 (s, 18H); $^{13}$C NMR (100 MHz, $CD_2Cl_2$): δ 164.7 (CH), 139.0 (C), 137.0 (CH), 134.5 (CH), 130.2 (CH), 129.9 (CH), 126.6 (C), 62.1 ($CH_2$), 55.1 (C), 28.7 ($CH_3$), 28.3 ($CH_2$).

$RuCl_2$(XXXIII)

Isomer 1: $^1$H NMR (400 MHz, $CD_2Cl_2$): δ 8.50 (s, 2H), 7.70-7.59 (m), 7.59-7.42 (m), 7.42-7.25 (m), 4.95 (d, $J_{HH}$=11 Hz, 2H), 3.48 (d, $J_{HH}$=11 Hz, 2H), 1.32 (s, 18H), 1.15 (s, 6H); $^{13}$C NMR (100 MHz, $CD_2Cl_2$): δ 165.1 (CH), 138.9 (C), 137.1 (CH), 134.6 (CH), 130.3 (CH), 129.9 (CH), 126.4 (C), 75.1 ($CH_2$), 55.1 (C), 36.4 (C), 28.7 ($CH_3$), 26.1 ($CH_3$).

Isomer 2: $^1$H NMR (400 MHz, $CD_2Cl_2$): δ 8.42 (s, 2H), 7.70-7.59 (m), 7.59-7.42 (m), 7.42-7.25 (m), 5.24 (d, $J_{HH}$=11 Hz, 2H), 3.51 (d, $J_{HH}$=11 Hz, 2H), 1.38 (s, 18H), 1.13 (s, 6H); $^{13}$C NMR (100 MHz, $CD_2Cl_2$): δ 166.2 (CH), 139.5 (C), 136.6 (CH), 134.3 (CH), 129.9 (CH), 129.7 (CH), 129.2 (C), 76.7 ($CH_2$), 55.0 (C), 36.2 (C), 29.3 ($CH_3$), 27.3 ($CH_3$).

(R,R)—$RuCl_2$(XXXIV)

$^1$H NMR (400 MHz, $CD_2Cl_2$): δ 8.94 (s, 2H), 8.78 (d, $J_{HH}$=2.7 Hz, 2H), 8.06 (dd, $J_{HH}$=8.5, 2.7 Hz, 2H), 7.62 (d, $J_{HH}$=8.5 Hz, 2H), 3.64-3.53 (m, 2H), 1.99-1.71 (m, 6H), 1.61-1.47 (m, 2H), 1.16 (s, 18H); $^{13}$C NMR (100 MHz, $CD_2Cl_2$): δ 159.8 (CH), 148.9 (C), 140.8 (C), 138.5 (CH), 131.9 (C), 130.5 (CH), 124.8 (CH), 72.5 (CH), 58.4 (C), 31.8 ($CH_2$), 29.0 ($CH_3$), 24.7 ($CH_2$).

(R,R)—$RuCl_2$(XXXV)

$^1$H NMR (400 MHz, $CD_2Cl_2$): δ 8.50 (s, 2H), 7.47-7.32 (m, 2H), 7.10-6.97 (m, 2H), 6.86-6.68 (m, 2H), 3.96-3.74 (m, 2H), 3.09 (s, 12H), 2.77-2.57 (m, 2H), 2.07-1.76 (m, 4H), 1.38 (s, 18H), $^{13}$C NMR (100 MHz, $CD_2Cl_2$): δ 159.1 (CH), 151.5 (C), 137.8 (CH), 126.5 (C), 120.1 (CH), 111.8 (CH), 70.9 (CH), 55.3 (C), 40.3 ($CH_3$), 31.6 ($CH_2$), 29.4 ($CH_3$), 25.1 ($CH_2$).

(R,R)—$RuCl_2$(XXXVI)

$^1$H NMR (400 MHz, $CD_2Cl_2$): δ 8.86 (s, 1H), 8.67 (s, 1H), 7.83-7.69 (m, 2H), 7.69-7.50 (m, 6H), 4.56-4.40 (m, 1H), 4.28-3.93 (m, 2H), 1.68 (s, 3H), 1.37 (s, 18H); $^{13}$C NMR (100 MHz, $CD_2Cl_2$): δ 162.8 (CH), 138.8 (C), 138.7 (C), 137.6 (CH), 137.5 (CH), 136.4 (CH), 135.8 (CH), 132.4 (CH), 132.3 (CH), 130.9 (CH), 130.7 (CH), 130.0 (CH), 129.9 (CH), 129.0 (CH), 128.8 (CH), 125.6 (C), 125.1 (C), 71.9 ($CH_2$), 56.2 (C), 29.1 ($CH_3$), 29.1 ($CH_3$).

The invention claimed is:

1. A process for the reduction by hydrogenation, using molecular $H_2$, of a $C_3$-$C_{70}$ substrate containing one, two or three ketones and/or aldehydes functional groups into the corresponding alcohol, characterized in that said process is carried out in the presence of at least a base and at least one catalyst or pre-catalyst in the form of a $C_8$-$C_{56}$ ruthenium complex comprising in the coordination sphere a tetradentate ligand (L4) coordinating the ruthenium with:

two nitrogen atoms, each in the form of a primary or secondary amine (i.e. a $NH_2$ or NH group) or N-alkyl imine functional groups (i.e. a C=N group), and two sulfur atoms, each in the form of thioether functional groups.

2. A process according to claim 1, characterized in that said substrate is of formula $$R^a-C(=O)-R^b \quad (I)$$

wherein $R^a$ represents a hydrogen atom or a $R^b$ group; and $R^b$ represents a $C_1$-$C_{29}$ hydrocarbon group optionally substituted and optionally comprising one or two carbonyl groups, a $C_1$-$C_6$ hydrocarbon group substituted by a $C_{3-8}$ heterocycle (aromatic or not) comprising one or two atoms selected amongst sulfur, nitrogen or oxygen, or a $C_{3-8}$ heterocycle (aromatic or not) comprising one or two atoms selected amongst sulfur, nitrogen or oxygen optionally substituted by one or two $C_1$-$C_6$ hydrocarbon group;

$R^a$ and $R^b$ are bonded together and form a $C_3$-$C_{20}$, preferably $C_4$-$C_{20}$, saturated or unsaturated hydrocarbon group, optionally substituted and optionally comprising one or two carbonyl groups.

3. A process according to claim 1, characterized in that said substrate is of formula (I)

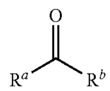

wherein $R^a$ represents a hydrogen atom or a $C_1$-$C_{28}$ hydrocarbon group, optionally substituted; and $R^b$ represents, a $C_1$-$C_{29}$ hydrocarbon group, optionally substituted and optionally comprising one or two carbonyl groups; or represents a $C_{3-8}$ heterocycle (aromatic or not) comprising one or two atoms selected amongst sulfur, nitrogen or oxygen;

$R^a$ and $R^b$ are bonded together and form a $C_3$-$C_{20}$, preferably $C_4$-$C_{20}$, saturated or unsaturated hydrocarbon group, optionally substituted and optionally comprising one or two carbonyl groups;

and the optional substituents of $R^a$ and $R^b$ are one, two, or three halogen, $OR^c$, $NR^c_2$, $SR^c$, groups, in which $R^c$ is a hydrogen atom, a halogenated $C_1$-$C_2$ group or a $C_1$ to $C_{10}$ cyclic, linear or branched alkyl or alkenyl group, preferably a $C_1$ to $C_4$ linear or branched alkyl or alkenyl group.

4. A process according to claim 1, characterized in that said base is a $C_{1-8}$ alkoxide, an alkaline or alkaline-earth hydroxide, or an inorganic hydride.

5. A process according to claim 1 characterized in that said ruthenium complex is of formula $$[Ru(L4)(L)_{2-r}Y_r](Z)_{2-r} \quad (1)$$

wherein r represents 0, 1 or 2;

L4 represents one $C_{10-40}$ tetradentate ligand coordinating the Ru metal with:

two nitrogen atoms, each in the form of a primary or secondary amine (i.e. a $NH_2$ or NH group) or N-alkyl imine functional groups (i.e. a C═N group), and two sulfur atoms, each in the form of thioether functional groups; and each L represents, simultaneously or independently, a neutral $C_1$-$C_{26}$ neutral monodentate ligand;

each Y represents, simultaneously or independently, a halogen atom, a hydrogen atom, a $BH_4$ group, a hydroxyl group, a $C_1$-$C_{10}$ alkoxyl group or an $C_3$-$C_{15}$ alkyl group;

each Z represents, simultaneously or independently, $ClO_4^-$, $BF_4^-$, $PF_6^-$, $SbCl_6^-$, $AsCl_6^-$, $SbF_6^-$, $AsF_6^-$, a $R^dSO_3^-$ wherein $R^d$ is a chlorine of fluoride atom or an $C_1$-$C_8$ alkyl, aryl, fluoroalkyl or fluoroaryl group, or a $BR^e_4^-$ wherein $R^e$ is a phenyl group optionally substituted by one to five groups such as halide atoms and/or methyl and/or $CF_3$ groups.

6. A process according to claim 5, characterized in that said ligand L4 is of formula (A)

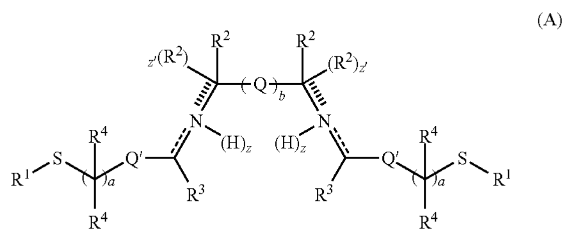

wherein a is 0 or 1, b is 0 or 1;

each z and z' is 1, in which case the all dotted and hatched lines represent a single bond (amino group); or z' is 1 and z is 0, in which case the all hatched lines represent a single bond and all dotted lines represent a double bond (imino group); or z' is 0 and z is 1, in which case the all dotted lines represent a single bond and all hatched lines represent a double bond (imino group); and each $R^1$ represents a linear, branched or cyclic $C_1$ to $C_{12}$ alkyl or alkenyl group optionally substituted or an $C_{6-10}$ aromatic group optionally substituted; and each $R^2$ represents a hydrogen atom, a $C_{1-10}$ alkyl or alkenyl group optionally substituted or a $C_{6-10}$ aromatic group optionally substituted; two adjacent $R^2$, taken together, may form a saturated or unsaturated cycle containing 5 to 12 atoms and including the atoms to which said $R^2$ are bonded, and being optionally substituted;

each $R^3$ represents a hydrogen atom or a $C_{1-10}$ alkyl or alkenyl group optionally substituted or a $C_{6-10}$ aromatic group optionally substituted;

each $R^4$ represents a hydrogen atom, a $C_{1-10}$ alkyl or alkenyl group optionally substituted or a $C_{6-10}$ aromatic group optionally substituted;

each Q' represents a $C_{10}$-$C_{16}$ metallocenediyl, a diphen-2,2'-yl, a 1,1'-binaphthalene-2,2'-diyl, a benzene-1,2-diyl, a naphthalenediyl group optionally substituted; and Q represents a Q' group or a group of formula (i)

$$-\left[\overset{R^6}{\underset{R^5}{C}}\right]_m-$$

wherein m is 1 or 2 and each $R^5$ and $R^6$ represent, simultaneously or independently, a hydrogen atom, a $C_{1-10}$ alkyl or alkenyl group optionally substituted, a $C_{6-10}$ aromatic group optionally substituted; two distinct $R^6$ and/or $R^5$ groups, taken together, may form a $C_{3-8}$, or even up to $C_{10}$, saturated, unsaturated or aromatic ring optionally substituted, including the atoms to which said $R^6$ and/or $R^5$ groups are bonded, and the optional substituents of said $R^1$, $R^2$, $R^3$, $R^4$, $R^5$, $R^6$ or Q' are one, two, three or four groups selected amongst i) halogen atom (in particular when said substituents are on aromatic moieties), ii) $C_{5-12}$ cycloalkyl or cycloalkenyl, iii) $C_{1-10}$ alkoxy, alkyl, alkenyl, polyalkyleneglycols or halo- or perhalo-hydrocarbon, iv) a benzyl group or a fused or non-fused phenyl or indanyl group, said group being optionally substituted by one, two or three halogen, $C_{1-8}$ alkyl, alkoxy, or halo- or perhalo-hydrocarbon groups. The Q' group may also be substituted by one or two amino, nitro or sulfonate groups or by one or two groups of formula O—$(CR^8_2)_n$—O or O—$(CR^8_2)_n$—$NR^7$ wherein n is 1 or 2 and $R^8$ being a hydrogen atom or a $C_{1-4}$ alkyl group. The expression "halo- or perhalo-hydrocarbon" has here the usual meaning in the art, e.g. groups such as $CF_3$ or $CClH_2$ for instance.

7. A process according to claim 5, characterized in that said ligand L4 is of formula (B)

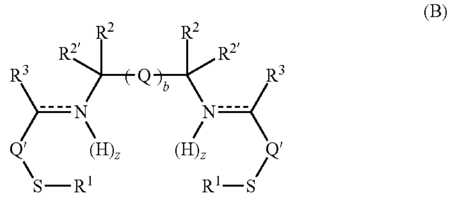

wherein b is 0 or 1;

each z is 1, in which case the all dotted lines represent a single bond (amino group); or z is 0, in which case the all dotted lines represent a double bond (imino group); and each $R^1$ represents, a linear, branched or cyclic $C_1$ to $C_{10}$ alkyl group optionally substituted or a $C_{6-10}$ aromatic group optionally substituted; and each $R^2$ or $R^{2'}$ represents a hydrogen atom, a $C_{1-6}$ alkyl or alkenyl group optionally substituted or a $C_{6-10}$ aromatic group optionally substituted; two adjacent $R^2$, or $R^2$ and $R^{2'}$, taken together, may form a saturated or unsaturated cycle containing 5 to 6 atoms and including the atoms to which said $R^2$ or $R^{2'}$ are bonded, and being optionally substituted;

each $R^3$ represents a hydrogen atom or a $C_{1-6}$ alkyl group optionally substituted;

each Q' represents a 2,2'-diphenyl, a 1,1'-binaphthalene-2,2'-diyl, a benzene-1,2-diyl, a naphthalene-1,2-diyl or a naphthalene-2,3-diyl group optionally substituted; and Q represents a Q' group or a group of formula (i)

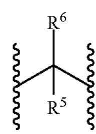

wherein $R^5$ and $R^6$ represent, simultaneously or independently, a hydrogen atom, a $C_{1-6}$ alkyl or alkenyl group optionally substituted, or a phenyl group optionally substituted; two distinct $R^6$ and/or $R^5$ groups, taken together, may form a $C_{3-6}$ saturated or unsaturated ring optionally substituted, including the atoms to which said $R^6$ and/or $R^5$ groups are bonded, and the optional substituents of said $R^1$, $R^2$, $R^{2'}$, $R^3$, $R^5$, $R^6$ or Q', in formula (B), are one, two or three groups selected amongst i) halogen atom (in particular when said substituents are on aromatic moieties), ii) $C_{5-6}$ cycloalkyl or cycloalkenyl, iii) $C_{1-6}$ alkoxy, alkyl or perhalo-hydrocarbon, iv) a benzyl group or a fused or non-fused phenyl or indanyl group, said group being optionally substituted by one, two or three halogen, $C_{1-4}$ alkyl or alkoxy, groups.

8. A process according to claim 5, characterized in that ligand L4 is of formula (C)

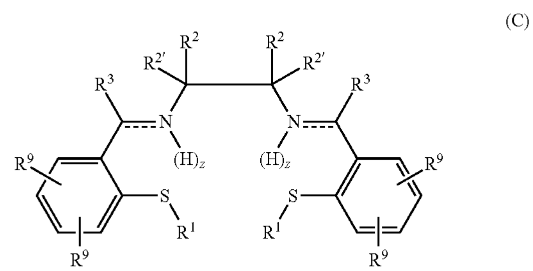

wherein each z is 1, in which case the all dotted lines represent a single bond (amino group); or z is 0, in which case the all dotted lines represent a double bond (imino group); and each $R^1$ represents, a linear, branched or cyclic $C_1$ to $C_{10}$ alkyl group optionally substituted or a $C_{6-10}$ aromatic group optionally substituted; and each $R^2$ or $R^{2'}$ represents a hydrogen atom, a $C_{1-6}$ alkyl or alkenyl group optionally substituted or a $C_{6-10}$ phenyl group optionally substituted; two adjacent $R^2$, or $R^2$ and $R^{2'}$, taken together, may form a saturated or unsaturated cycle containing 5 to 6 atoms and including the atoms to which said $R^2$ or $R^{2'}$ are bonded, and being optionally substituted;

each $R^3$ represents a hydrogen atom or a $C_{1-6}$ alkyl group optionally substituted; and each $R^9$ represents a hydrogen atom, a halogen atom, such as Cl or F, a $C_{1-6}$ alkoxy, alkyl or perhalo-hydrocarbon, or a benzyl or phenyl group optionally substituted; or two adjacent $R^9$ bonded to the same benzene ring, taken together, represents a fused phenyl or indanyl group, said group being optionally substituted by one, two or three halogen, $C_{1-4}$ alkyl or alkoxy groups, and the optional substituents of said $R^1$, $R^2$, $R^{2'}$, $R^3$ or $R^9$, in formula (C), are one or two groups selected amongst i) halogen atom (in particular when said substituents are on aromatic moieties), ii) $C_{1-6}$ alkoxy, alkyl or perhalo-hydrocarbon.

9. A ruthenium complex of formula (1), $$[Ru(L4)(L)_{2-r}Y_r](Z)_{2-r} \quad (1)$$

wherein:

r represents 0, 1 or 2;

L4 represents one $C_{10-40}$ tetradentate ligand coordinating the Ru metal with:

two nitro en atoms each in the form of a primary or secondary amine (i.e. a $NH_2$ or NH group) or N-alkyl imine functional groups (i.e. a C═N group), and two sulfur atoms, each in the form of thioether functional groups; and each L represents, simultaneously or independently, a neutral $C_1$-$C_{26}$ neutral monodentate ligand;

each Y represents, simultaneously or independently, a halogen atom, a hydrogen atom, a $BH_4$ group, a hydroxyl group, a $C_1$-$C_{10}$ alkoxyl group or an $C_3$-$C_{15}$ allyl group;

each Z represents, simultaneously or independently, $ClO_4^-$, BF4-, PF6-, SbCl6-, AsCl6-, SbF6-, AsF6-, a $R^dSO_3^-$ wherein $R^d$ is a chlorine of fluoride atom or an $C_1$-$C_8$ alkyl, aryl, fluoroalkyl or fluoroaryl group, or a $BR^3_4{}^-$ wherein $R^e$ is a phenyl group optionally substituted by one to five groups such as halide atoms and/or methyl and/or $CF_3$ groups, provided that the complexes N,N'-bis(2-(tert-butylthio-κS)benzylidene)-1,2-ethanediamino-κN,κN')dichlororuthenium(II), (N,N'-bis(2-(tert-butylthio-κS)benzylidene)-1,2-cyclohexyldiamino-κN,κN') dichlororuthenium(II), N,N'-bis(2-(tert-butylthio-κS) benzylidene)-1,3-propanediamino-κN,κN') dichlororuthenium(II) and N,N'-bis(2-(tert-butylthio-κS)benzylidene)-1,2-propanediamino-κN,κN') dichlororuthenium(II) are excluded.

* * * * *